(12) United States Patent
Du et al.

(10) Patent No.: US 11,299,463 B2
(45) Date of Patent: Apr. 12, 2022

(54) PROCESS FOR THE MANUFACTURE OF PYRAZOLES OR PYRIMIDONES

(71) Applicant: Fujian Yongjing Technology Co., Ltd., Fujian (CN)

(72) Inventors: Hongjun Du, Fujian (CN); Wenting Wu, Fujian (CN)

( * ) Notice: Subject to any disclaimer, the term of this patent is extended or adjusted under 35 U.S.C. 154(b) by 32 days.

(21) Appl. No.: 16/517,542

(22) Filed: Jul. 20, 2019

(65) Prior Publication Data
US 2020/0140390 A1 May 7, 2020

(30) Foreign Application Priority Data

Nov. 7, 2018 (DE) .......................... 102018127849.7

(51) Int. Cl.
*C07D 231/20* (2006.01)
*C07D 231/14* (2006.01)
*C07D 239/47* (2006.01)

(52) U.S. Cl.
CPC ......... *C07D 231/20* (2013.01); *C07D 231/14* (2013.01); *C07D 239/47* (2013.01)

(58) Field of Classification Search
CPC .................................................. C07D 231/20
See application file for complete search history.

(56) References Cited

U.S. PATENT DOCUMENTS 3,219,550 A 11/1965 Horvitz

FOREIGN PATENT DOCUMENTS

| CN | 101824000 | 7/2012 |
|---|---|---|
| CN | 107652237 | 2/2018 |
| EP | 1637271 | 5/2011 |
| JP | 2015155399 | 8/2015 |
| JP | 2017039722 | 2/2017 |
| WO | WO2007043677 | 4/2007 |
| WO | WO2008022777 | 2/2008 |
| WO | WO2008/101976 | 8/2008 |
| WO | WO2009106230 | 9/2009 |
| WO | WO2009135808 | 11/2009 |
| WO | WO2010037688 | 4/2010 |
| WO | WO201 2025469 | 3/2012 |
| WO | WO2012065932 | 5/2012 |
| WO | WO2012065945 | 5/2012 |
| WO | WO2013167586 | 11/2013 |
| WO | WO2014038224 | 3/2014 |
| WO | WO2016205460 | 12/2016 |
| WO | WO2017012965 | 1/2017 |
| WO | WO2018024644 | 2/2018 |

OTHER PUBLICATIONS

Gomez et al., Analytical Chemistry (2015), 87, pp. 10547-10555.*
Wiles et al. Organic Process Research & Development (2004), 8, pp. 28-32.*

* cited by examiner

*Primary Examiner* — Paul V Ward

(57) ABSTRACT

In one aspect the invention relates to the use of an amine compound in a process for the manufacture of a fluorinated or non-fluorinated 5- or 6-membered heterocyclic compound containing two nitrogen atoms in the ring system of the said compound, preferably of pyrazoles or pyrimidones. The invention also relates to a process for the manufacture of pyrazoles or pyrimidones, which may be fluorinated or may not be fluorinated (non-fluorinated). Especially, the invention relates to process for the manufacture of fluorinated pyrazoles or pyrimidones, and in particular the invention relates to process for the manufacture of such fluorinated pyrazoles or pyrimidones, which each are very important building blocks for pharmaceutical and agro-applications. For example, the fungicides are Bixafen, Fluxapyroxad, Fluindapyr, Sedaxane, Isopyrazam and Benzovindifupyr strongly depend on such fluorinated pyrazoles as key building blocks, or for Florasulam and Clorasulam-methyl (Diclosulam), respectively.

13 Claims, 3 Drawing Sheets

PROCESS FOR THE MANUFACTURE OF PYRAZOLES OR PYRIMIDONES

BACKGROUND OF THE INVENTION

Field of the Disclosure

In one aspect the invention relates to the use of an amine compound in a process for the manufacture of a fluorinated or non-fluorinated 5- or 6-membered heterocyclic compound containing two nitrogen atoms in the ring system of the said compound, preferably of pyrazoles or pyrimidones. The invention also relates to a process for the manufacture of pyrazoles or pyrimidones, which may be fluorinated or may not be fluorinated (non-fluorinated). Especially, the invention relates to process for the manufacture of fluorinated pyrazoles or pyrimidones, and in particular the invention relates to process for the manufacture of such fluorinated pyrazoles or pyrimidones, which each are very important building blocks for pharmaceutical and agro-applications. For example, the fungicides are Bixafen, Fluxapyroxad, Fluindapyr, Sedaxane, Isopyrazam and Benzovindifupyr strongly depend on such fluorinated pyrazoles as key building blocks, or for Florasulam and Clorasulam-methyl (Diclosulam), respectively.

Description of Related Art

A typically important non-fluorinated pyrazole is DMPO (2,4-dihydro-2,5-dimethyl-3H-pyrazol-3-one).

A growing number of fluorine-containing active ingredients in the pharmaceutical and agrochemical industries inevitably raises the demand for new fluorinated building blocks. Their availability is mainly constricted by suitable chemistry and available bulk fluorine containing starting materials. Because of the high cost impact especially in the agrochemical industry, the choice of a synthetic route is heavily driven by economic aspects; thus, the environmental profile often is handled as a "secondary factor" or finally falls aside. DFMMP (3-(difluoromethyl)-1-methyl-1H-pyrazole-4-carboxylic acid ethyl ester or ethyl 3-(difluoromethyl)-1-methyl-1H-pyrazole-4-carboxylic acid) is a key building block for a fast growing new fungicide family, like Syngenta's Sedaxane, and BASF's Fluxapyroxad and Bayer's Bixafen currently made by environmentally less friendly routes. Herein the present has as an objective to provide a cost-competitive and green route displaying significantly lower environmental impact than the said processes known in the prior art.

An atom-efficient route to ethyl 3-(difluoromethyl)-1-methyl-1H-pyrazole-4-carboxylate (DFMMP), which is a key building block for a novel fungicide family is scientifically described by J. Jaunzems and M. Braun in Organic Process Research & Development (OPRD 2014, 18, 1055-1059), and is displayed in the following Reaction Scheme A:

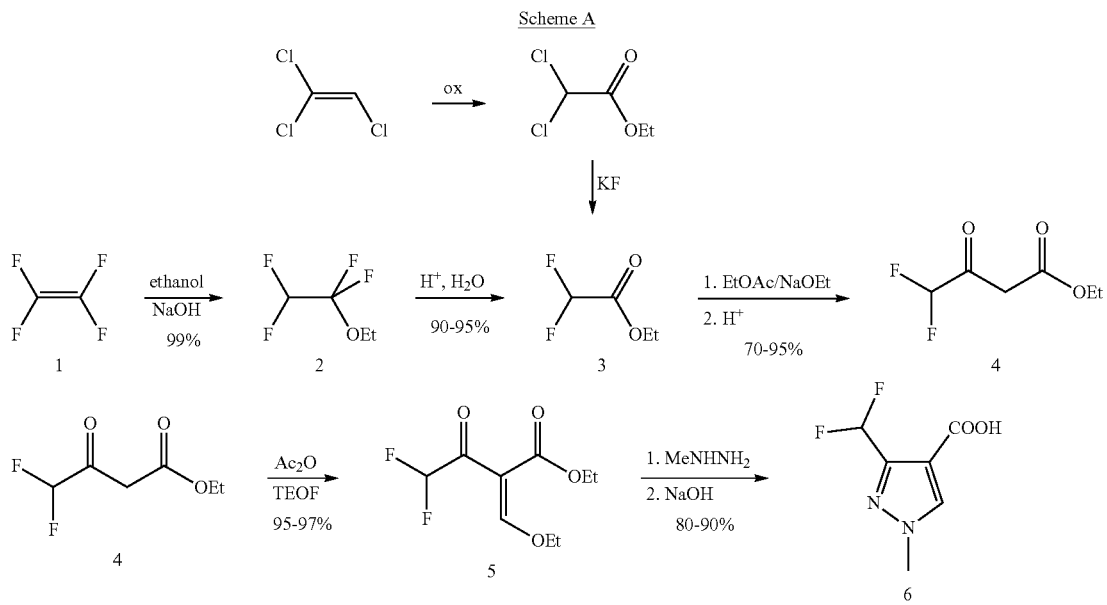

In Scheme A the following meanings shall apply: compound (1) is tetrafluoroethylene (TFE); (2) represents an intermediate compound; compound (3) is ethyl-2,2-difluoroacetate (EDFA); compound (4) is ethyl difluoracetoacetate; (5) represents an α,β-unsaturated ketone compound; Ox=oxidation; TEOF=triethylorthoformiate; MeNHNH$_2$=Monoethylhydrazin (MMH).

The compound (6) in the scheme represents DFMPA (3-(difluoromethyl)-1-methyl-1H-pyrazole-4-carboxylic acid; sometimes also abbreviated as "DFPA"), and the intermediate compound advancing DFMPA (6) in this synthesis is always the compound DFMMP (ethyl 3-(difluoromethyl)-1-methyl-1H-pyrazole-4-carboxylate), e.g., as displayed in the following Reaction Scheme B:

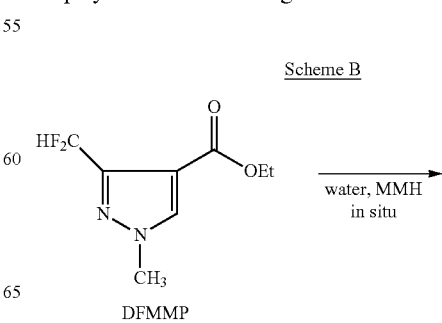

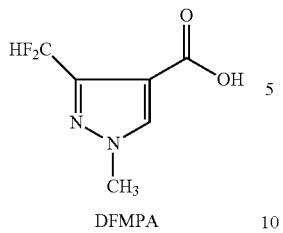

DFMPA

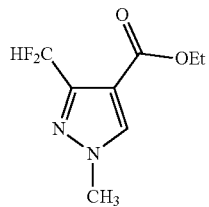

DFMMP

MMH=Monomethylhydrazin

DFMMP: ethyl 3-(difluoromethyl)-1-methyl-1H-pyrazole-4-carboxylate or alternatively 3-(difluoromethyl)-1-methyl-1H-pyrazole-4-carboxylic acid ethyl ester DFMPA: 3-(difluoromethyl)-1-methyl-1H-pyrazole-4-carboxylic acid For example, a number of production methods are known in conventional batch or continuously operated reactors from WO 2014/038224 A1, WO 2008/022777 A1, and WO 2012/025469 A1.

The international patent publication WO 2014038224 describes a synthesis of the DFMMP starting from EEMD-FAA (ethyl 2-ethoxymethylene-4,4-difluoroacetoacetate or 3-(difluoromethyl)-1-methyl-1H-pyrazole-4-carboxylic acid ethyl ester) in 92.8% yield, with hydrous MMH (e.g., using MMH in water), 40-95 wt % organic solvent content in the reactor, as batch process. For industrial production the process is only conditionally feasible due to very long reaction time (residence time) and necessary solvent recycling. Disadvantageously, MMH (Monomethylhydrazin) and derivatives end up in the reaction effluent. Since hydrous MMH is used, the stated yield of 92.8% of DFMMP is questionable. Also, according to authors, the material is contaminated with 2.6% of the unwanted regioisomer.

In the international patent publication WO 2008/022777 A2, there the state of the art is well described regarding the synthesis of the difluorinated part of the pyrazole compounds of interest starting from tetrafluoroethylamine (TFEA).

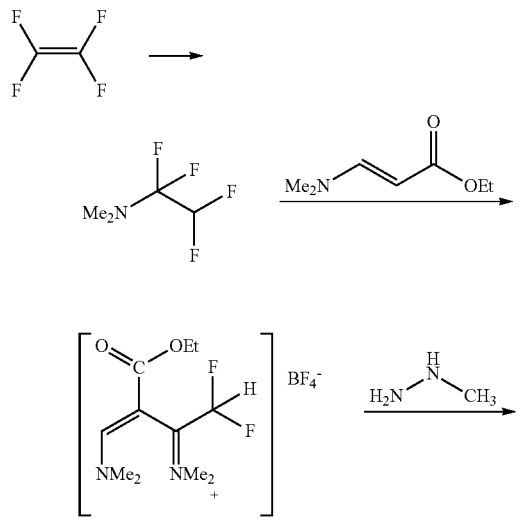

Thus, the WO 2008/022777 A2 relates to a process for preparing 3-dihalomethylpyrazole-4-carboxylic acid derivatives by reacting α-fluoroamines in the presence of Lewis acids, with acrylic acid derivatives to give vinamidinium salts and subsequently reacting them with hydrazines, and especially to the vinamidinium salts themselves as intermediates.

Finally, the international patent publication WO 2012/025469 A1 describes an improved process for the preparation of esters of 1-H-pyrazole-4-carboxylic acids, using e.g. water-free MMH in pentafluorobutane (365mfc) as a solvent in a batch process. Thus, the WO 2012/025469 A1 relates to a process for the manufacture of an ester of a 1-H-pyrazole-4-carboxylic acid of formula (I) wherein—R1 is H or an organic residue—R2 is H or an organic residue—R3 is H, an alkyl group having from 1 to 12 carbon atoms, an halogenated alkyl group having from 1 to 12 carbon atoms, an aralkyl group, an aryl group, a halogen, which comprises reacting a compound of formula (7): wherein R4 is C1-C8-alkyl, C3-C8-cycloalkyl, C2-C8-alkenyl, benzyl or phenyl, R1 and R3, are as defined above with a hydrazine of formula R2NHNH2 wherein R2 is as defined above, in the presence of an organic solvent comprising at least one halogen, e.g., in pentafluorobutane (365mfc).

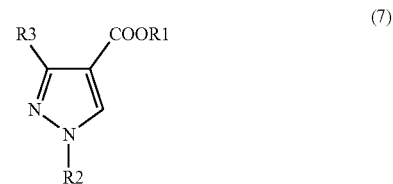

However, very few methods are suitable for the industrial scale because, firstly, in the process route using tetrafluoroethylene as the starting material in the resulting pyrazole just only 2 of the original 4 fluorine atoms remain and especially the formation of the pyrazole ring with corresponding hydrazine precursors is very exothermic, and secondly, on the other hand for safety reasons in the industrial scale the process route is performed only with hydrous monomethylhydrazine (hydrous MMH, this is usually only a 40% solution of methylhydrazine in water), since, for example, MMH is also used in place of 1,1-dimethylhydrazine as a storable rocket fuel along with the oxidant dinitrogen teroxide. In addition, regarding MMH the classification for MMH (methylhydrazine) was amended by the European Chemicals Agency (ECHA) Committee on Risk Assessment (RAC) on 11 Sep. 2018 as follows: methylhydrazine is classified as carcinogenic Carc 1B; any MMH residues of reactions such as those possibly formed and described e.g. in the cyclization of appropriate precursors to the pyrazoles must be advantageously avoided in the water. Source: GESTIS Substance Database: http://gestis.trust.de/nxt/gateway.dll/gestis_de/
510635.xml?f=templates$fn=default.html.$3.0), wherein for example MMH (methylhydrazine) is described as a hazardous compound involved in dangerous chemical reactions: Risk of explosion in contact with lead, iron oxides, copper oxides, and manganese. The substance can react dangerously with fluorine, strong oxidants, nitric acid, hydrogen peroxide, chlorine trifluoride, porous Also, in the cyclization of unsymmetrical hydrazines, almost always, after in situ saponification of the pyrazole ester, which always occurs as an intermediate, a pyrazole regioisomer is formed, albeit in small quantities, which is, interestingly, more water-soluble than the desired pyrazole products. The better water solubility of the unwanted regioisomer, without intending to be bound by theory, could be due to the fact that lipophilic alkyl groups such as, for example, perfluoroalkyl, $CF_3$, $CF_2H$, $CF_2Cl$, $CFH_2$ are then positioned together with the N-substituted lipophilic alkyl radical, and hence the molecule undergoes a higher polarization. Also, due to this better water solubility of regioisomers water of reaction and wastewater can become contaminated with hydrazine and derivatives. For illustration, the undesired and desired regioisomers are displayed hereunder in Scheme C, with representative substituents, see Scheme C:

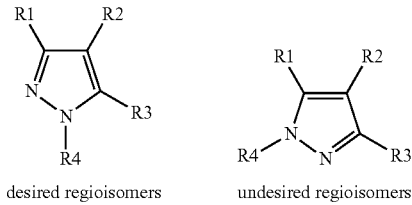

Scheme C desired regioisomers    undesired regioisomers

Herein the residues R1, R2, and R3 have the meaning as defined herein further below.

Processes for the manufacture of pyrazoles are already known in the prior art, as shown by the following representative methods.

The current state of the art has a number of disadvantages. None of the known methods referenced herein before provides pyrazolesin industrial yields. Also, the known methods are not resources and energy saving because of their poor selectivity and high energy consumption e.g. for solvent removal and solvent recycling and if DFMMP is isolated, by a required purification by distillation even if DFMPA (but not the unwanted regioisomer which stays in the (waste) water) cristallizes out of much water containing reaction mixtures due to usage of MMH in water as raw material.

Therefore, it is an object of the present invention to provide a process for the manufacture of pyrazoles that industrially feasible, e.g. easily scalable to industrial yields of pyrazoles, and which process in particular shows improved (e.g. good) selectivity and low energy consumption for the targeted products. In particular, it is also an object of the present the invention to provide such an improved and/or optimized process for the manufacture of pyrazoles wherein the produced pyrazoles can be easily, e.g. by a method with only low energy consumption, purified and/or isolated, and wherein preferably the process for purifying and/or isolating does not require a distillation.

The objects of the invention are solved as defined in the claims and/or embodiments, and described herein after in detail. In particular, the present invention employs in preferred embodiments one or more microreactors in the concerned processes of the invention, i.e. in a process for the manufacture of pyrazoles and/or in the present invention employs in preferred embodiments one or more phase separation method.

SUMMARY OF THE INVENTION

In a first aspect the present invention solves the problems of the prior art by the use of an amine compound of formula (I), R4-NH—X, and/or a monohydrate thereof, wherein
  R4 denotes H or a branched or non-branched C1-C4 alkyl group, and
  X denotes a NH2 group or C(=NH)—OR5 group, wherein R5 denotes a branched or non-branched C1-C4 alkyl group,
in a process for the manufacture of a fluorinated or non-fluorinated 5- or 6-membered heterocyclic compound containing two nitrogen atoms in the ring system of the said compound, comprising a steps of feeding the said amine compound into at least one continuous flow reactor with upper lateral dimensions of up to about 1 cm, preferably with upper lateral dimensions of up to about ≤5 mm, preferably into at least one microreactor, and therein reacting the said amine compound with a carbonyl group containing three ring-carbon-atom precursor compound for the fluorinated or non-fluorinated 5- or 6-membered heterocyclic compound containing two nitrogen atoms in the ring system.

The process according to the present invention provides several advantages regarding the following criticalities of the prior state of the art: The possibility of contamination of reaction wastewater and thus wastewater containing water is avoided according to the invention by the use of generally by using less amount of water, and by using in preferred embodiments anhydrous hydrazines, especially methylhydrazine (MMH) as an example. Also, for safety reasons, anhydrous methylhydrazine (MMH) should once only be present in small amounts in the pyrazole formation reaction, requirement which the invention is well compliant with, and, because of the exothermicity during the cylization, in contrast to the invention, in the prior art the anhydrous methylhydrazine (MMH) can be only reacted in particularly costly and expensive reactors.

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to a microreactor, In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm.

Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behavior of chemical reactors of such design, so that key reactor variables, such as the dimensions of the reactor, can be estimated.

Fluid going through a PFR may be modelled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, for example, hydrazine×HCl (hydrazine hydrochloride), then the said solid raw materials are dissolved in an inert solvent. A preferred solvent is acetonitrile.

The present invention pertains in an embodiment to the preparation of fluorinated or non-fluorinated pyrazoles in one or more, preferentially pipe-like, continuous flow reactors with an hydrazine precursor and an α,β-unsaturated ketone compound, optionally with an anhydrous hydrazine precursor.

In a preferred embodiment the present invention pertains to the preparation of fluorinated or non-fluorinated pyrazoles, preferably in one or more microreactors, with an hydrazine precursor and an α,β-unsaturated ketone compound, with an anhydrous hydrazine precursor.

In certain embodiments of the present invention pertains to the preparation of fluorinated or non-fluorinated pyrazoles in one or more, preferentially pipe-like, continuous flow reactors, more preferably in one or more microreactors, wherein preferably an anhydrous hydrazine precursor is reacted with an α,β-unsaturated ketone to form the fluorinated or non-fluorinated pyrazole.

In the preparation of fluorinated or non-fluorinated pyrazoles in one or more, preferentially pipe-like, continuous flow reactors, more preferably in one or more microreactors, e.g. pyrazoles with and without fluorine, preferably with fluorine (fluorinated pyrazoles), the cyclization is controlled and continuous reaction in the said reactor or system, and optionally performed with anhydrous hydrazine precursors.

Information on possible starting materials and structures for pyrazoles, for example with fluorine: DFMMP, and for example, without fluorine: DMPO, is described in more detail herein below.

In an embodiment of the invention the starting material is DMPO, and the reaction thereof with MMH takes place with ketene generated in situ or with diketene in the microreactor, and is especially claimed as described herein and in the claims and/or embodiments.

In an embodiment a preferred fluorinated pyrazole manufactured according to the process of the invention is DFMMP (3-(difluoromethyl)-1-methyl-1H-pyrazole-4-carboxylic acid ethyl ester).

In an embodiment a preferred not fluorinated pyrazole manufactured according to the process of the invention is DMPO (2,4-dihydro-2,5-dimethyl-3H-pyrazol-3-one).

An experimental description for a MMH distillation is also described herein, or can be performed as known by those skilled in the field.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE INVENTION

The use and process according to the present invention provides several advantages regarding the following criticalities of the prior state of the art: The possibility of contamination of reaction wastewater and thus wastewater containing water is avoided according to the invention by the use of generally by using less amount of water, and by using in preferred embodiments anhydrous hydrazines, especially methylhydrazine (MMH) as an example. Also, for safety reasons, anhydrous methylhydrazine (MMH) should once only be present in small amounts in the steady state of the continuous pyrazole formation reaction, requirement which the invention is well compliant with, and, because of the exothermicity during the cylization, in contrast to the invention, in the prior art the anhydrous methylhydrazine (MMH) can be only reacted in particularly costly and expensive reactors.

Figure 1:
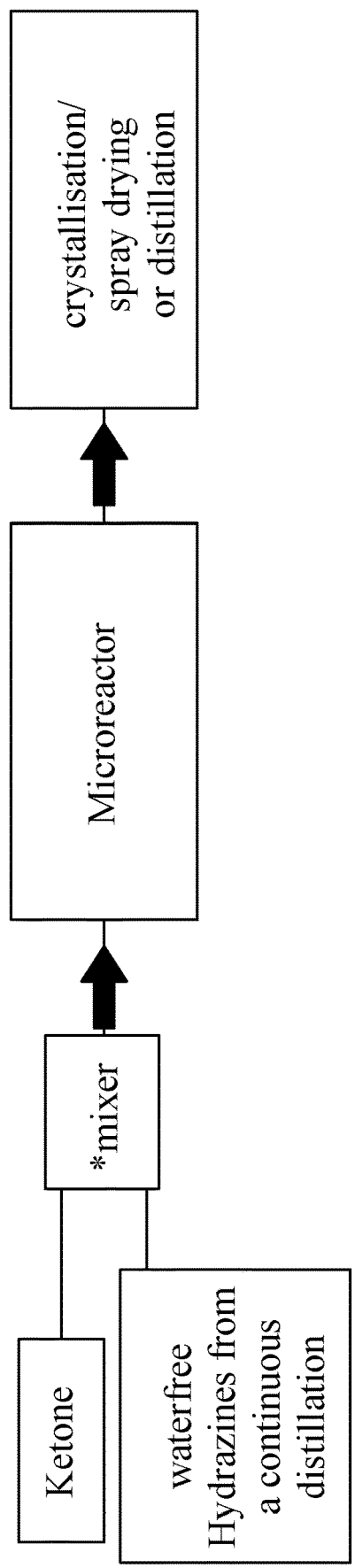
FIG. 1 shows, as an example and not intended to be limiting a reaction scheme for the continuous synthesis of pyrazoles according to the invention, for example, in a microreactor setting. The pyrazole compound obtained from the may be optionally subjected to a purification step, such as crystallization, spray drying and/or distillation. Also, the mixer shown for the mixing of the educts, may be a separate mixer (as shown) or may also additionally or alternatively be integrated into the microreactor. The hydrazines shown as an educt in the scheme are marked as waterfree, what is a preferred embodiment, i.e. it is not intended to limit to waterfree hydrazines.

By way of example, the invention shall be further described by reference to using a microreactor, but it is to be noted that thereby the invention is only described for a preferred embodiment of the invention, and that other, e.g. pipe-like, continuous flow reactor with upper lateral dimensions of up to about 1 cm, and as defined herein. Thus, such a continuous flow reactor preferably with upper lateral dimensions of up to about ≤5 mm, or of about ≤4 mm, refers to a preferred embodiment of the invention, e.g. preferably to a microreactor, FIG. 1 shows, as an example and not intended to be limiting a reaction scheme for the continuous synthesis of pyrazoles according to the invention, for example, in a microreactor setting. The pyrazole compound obtained from the may be optionally subjected to a purification step, such as crystallization, spray drying and/or distillation. Also, the mixer shown for the mixing of the educts, may be a separate mixer (as shown) or may also additionally or alternatively be integrated into the microreactor. The hydrazines shown as an educt in the scheme are marked as waterfree, what is a preferred embodiment, i.e. it is not intended to limit to waterfree hydrazines.

Figure 2:
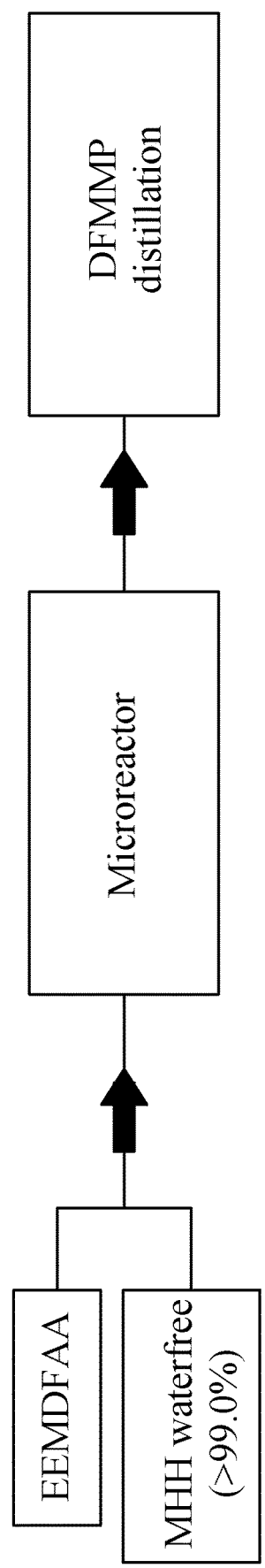
FIG. 2 shows the schematic process performed with MMH (waterfree, >99.0%), in a microreactor, as an example but not intended to be limited to this preferred embodiment. The resulting product DFMMP is purified by distillation, in this embodiment example.

FIG. 2 shows the schematic process performed with MMH (waterfree, >99.0%), in a microreactor, as an example but not intended to be limited to this preferred embodiment. The resulting product DFMMP is purified by distillation, in this embodiment example.

Figure 3:
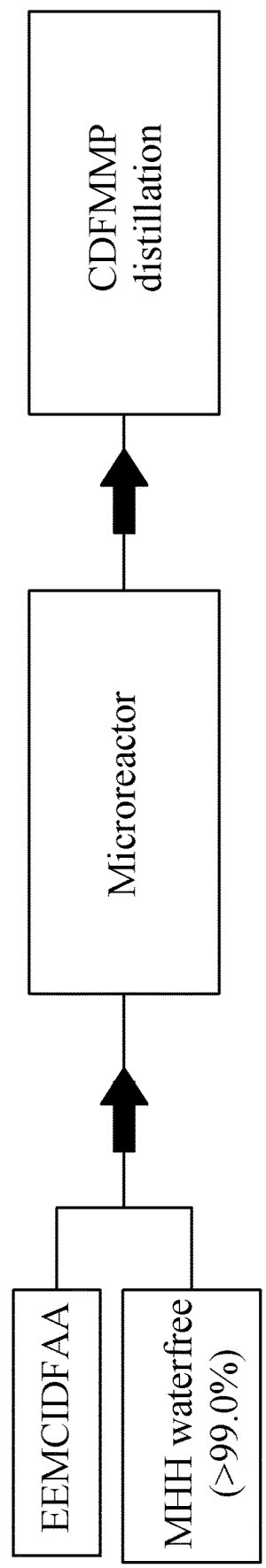
FIG. 3 shows the schematic process performed with MMH (waterfree, >98.0%), in a microreactor, as an example but not intended to be limited to this preferred embodiment. The resulting product CDFMMP is purified by distillation, in this embodiment example.

FIG. 3 shows the schematic process performed with MMH (waterfree, >98.0%), in a microreactor, as an example but not intended to be limited to this preferred embodiment. The resulting product CDFMMP is purified by distillation, in this embodiment example.

Both criteria, low local concentration and ideal removal of the heat generated by the exothermic heat is achieved by using a microreactor system with continuous operation. Interestingly, the choice of suitable reaction conditions in the microreactor, especially the temperature, the formation of the unnecessary regioisomers can be completely avoided.

Some example structures according to the invention are shown hereunder in the following Scheme C to illustrate structure examples of desired regioisomers obtainable in very good yields by the use and process of the invention, as compared to the undesired regioisomers, the formation thereof being widely suppressed or at least essentially diminished when employing the invention, see Scheme C:

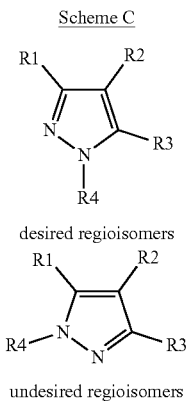

Scheme C desired regioisomers undesired regioisomers

Wherein, for example,

R1 represents, for example, alkyl, haloalkyl, perfluoralkyl; wherein in each independently the term "alkyl" denotes C1-C4-alkyl residue;

R2 represents, for example, H, $CO_2$-alkyl, $CO_2$-haloalkyl, $CO_2H$, F, Cl; wherein in each independently the term "alkyl" denotes C1-C4-alkyl residue;

R3 represents, for example, H, halogen, alkyl, haloalkyl; wherein in each independently the term "alkyl" denotes C1-C4-alkyl residue.

In an embodiment a preferred fluorinated pyrazole manufactured according to the process of the invention is DFMMP (3-(difluoromethyl)-1-methyl-1H-pyrazole-4-carboxylic acid ethyl ester).

In an embodiment a preferred not fluorinated pyrazole manufactured according to the process of the invention is DMPO (2,4-dihydro-2,5-dimethyl-3H-pyrazol-3-one).

The pyrazoles prepared according to the invention are very important synthesis building blocks for pharmaceutical and agro-applications. For example, the pyrazoles are very important synthetic building blocks for fungicides such as, in particular, bixafen, fluxapyroxad, fluindapyr, sedaxanes, isopyrazam and benzovindifupyr. The formation of non-desired regioisomers should be avoided or at least diminished as much as possible, preferably the formation of non-desired regioisomers should be substantially avoided or at least substantially diminished, more preferably the formation of non-desired regioisomers should be completely avoided. The various regioisomers of the fungicides bixafen, fluxapyroxad, fluindapyr, sedaxanes, isopyrazam and benzovindifupyr are shown in the following Scheme D:

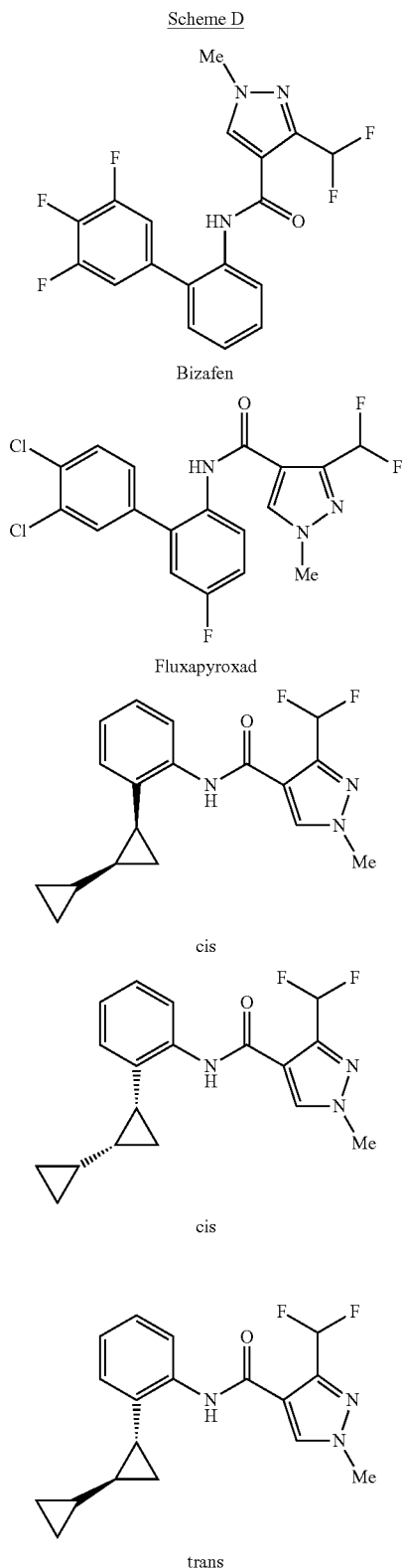

Bizafen

Fluxapyroxad cis cis trans

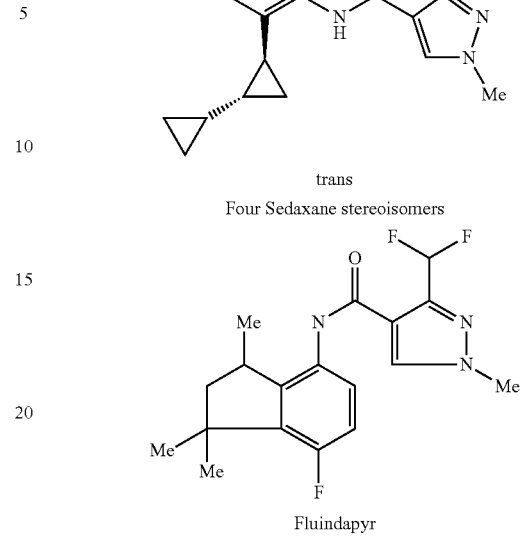

trans

Four Sedaxane stereoisomers

Fluindapyr

Further exemplary pyrazoles that can be prepared by the novel method according to the invention with MMH, preferably with anhydrous MMH, in one or more microreactors, in the following Schemes E to Q:

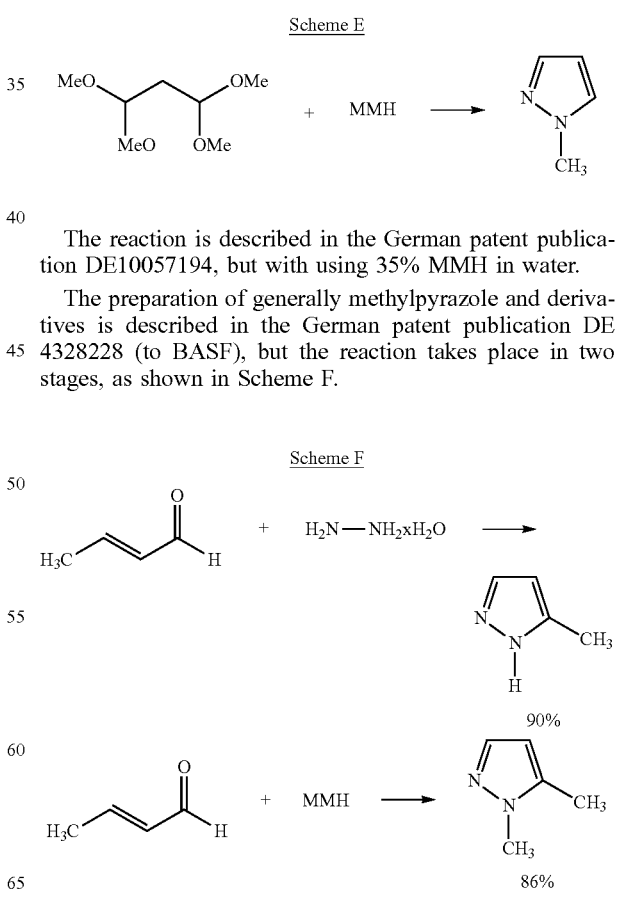

The reaction is described in the German patent publication DE10057194, but with using 35% MMH in water.

The preparation of generally methylpyrazole and derivatives is described in the German patent publication DE 4328228 (to BASF), but the reaction takes place in two stages, as shown in Scheme F.

If the reaction is carried out in the case of methylhydrazine with anhydrous MMH, the condensation is carried out, in a particular embodiment of the invention, in a microreactor in a single stage. In a particular embodiment of the invention, in the case of methylhydrazine with anhydrous MMH, the condensation reaction is carried out in a microreactor and without the addition of further reagents.

In the case of hydrazine, in a particular embodiment of the invention, in a microreactor, instead of the hydrazine hydrate, the $NH_2$—$NH_2 \times HCl$ salt is used which is previously taken up in solvent toluene or acetonitrile together with the crotonaldehyde at room temperature. The reaction times are reduced from the 2 h described in the batch reactor to a range of from about 30 sec to about at maximum 5 min in the microreactor.

When methyl vinyl ketone is used, reference is made to Bulletin of the Chemical Society of Japan (1991), 64 (2), 719-20, wherein a method is described that produces a regioisomer ratio of 50% of the desired isomer to 17% of the undesired isomer. The application of a controlled reaction in a microreactor eliminates the formation of the undesired 2,5-dimethylpyrazole, as shown in the following Scheme G.

Scheme G

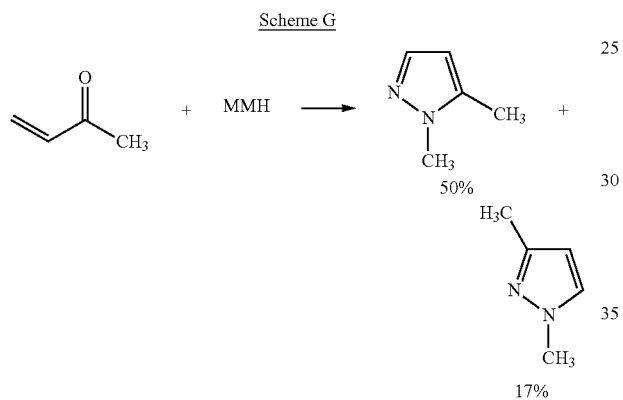

Faming Zhuanli Shenqing (2018), CN 107674028 A describes the reaction of MMH with acetoacetic ester. Here, the formation of the desired product, the 2,4-dihydro-2,5-dimethyl-3H-pyrazol-3-one (DMPO) is described being produced in 96% yield, but here also hydrous MMH is used and the reaction time is about 2 h. In the microreactor, the reaction can be performed with reduced reaction time of few minutes, for example reaction time can be reduced even to 1 min, as shown in the following Scheme H.

Scheme H

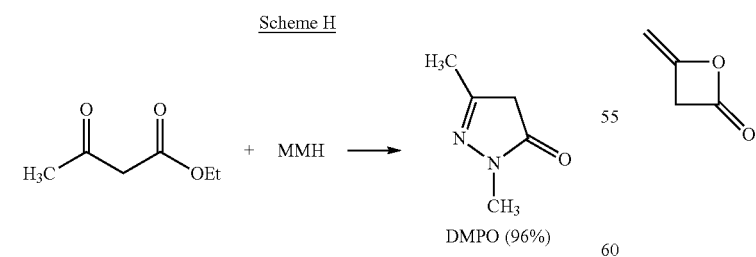

In the international patent publication WO 2016/205460 on page 52 the synthesis of DMPO is described even with reaction times of about 10 h with anhydrous MMH and quantitative conversion. Likewise the reaction with hydrazine in THF to MPO is described, as shown in the following Scheme I.

Scheme I

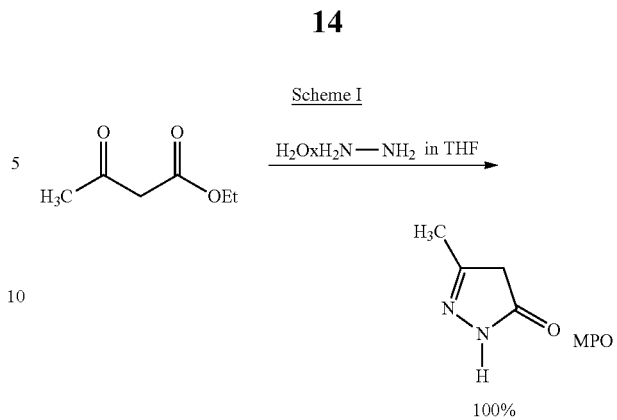

Somewhat earlier, in the journal Phosphorus, Sulfur and Silicon and the Related Elements (2017), 192 (1), 34-41 and by Wen, Yanpeng; Zhang, Shuang; Hou, Guangfeng; Yu, Yinghui; Gao, Jinsheng the same reaction was published in "Youji Huaxue" (Chinese Journal of Organic Chemistry) (2016), 36 (3), 642-647.

MPO synthesis is also reported in Faming Zhuanli Shenqing (2018), CN 107652237, as being produced in 91% yield, and in the International Journal of Pharmaceutical Sciences Review and Research (2016), 39 (2), 53-57 being produced in 90% yield and Synthetic Communications (2018), 48 (10), 1190-1198.

MPO and DMPO can also be prepared in water as solvent from diketene as described in Faming Zhuanli Shenqing (2018), CN 107652237 A Feb. 2, 2018, and as shown in the following Scheme J.

Scheme J

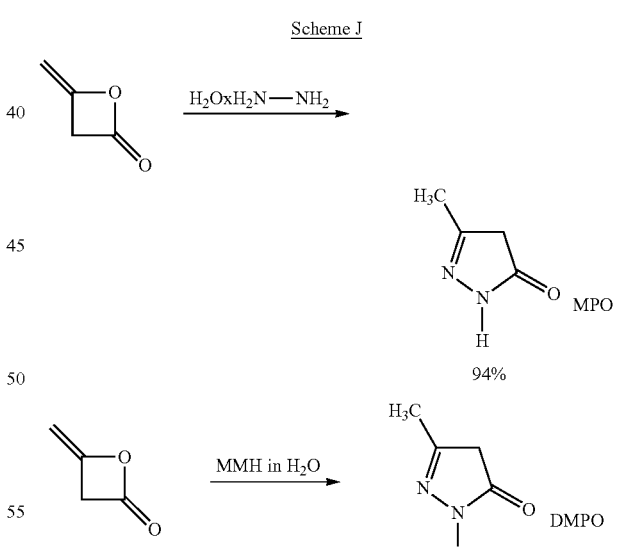

The common reaction principle for the preparation of 3-bromo and 3-chloro-pyrazoles is described very generally in Journal of Organic Chemistry (2018), 83 (5), 2830-2839, but wherein the 5-fluoropyrazoles and the educt (2,2,2-Trifluoroethylidene)-propanediacetic acid diethyl ester are not mentioned. For this reaction, to be performed according to the invention, reference is made following Scheme K.

Scheme K

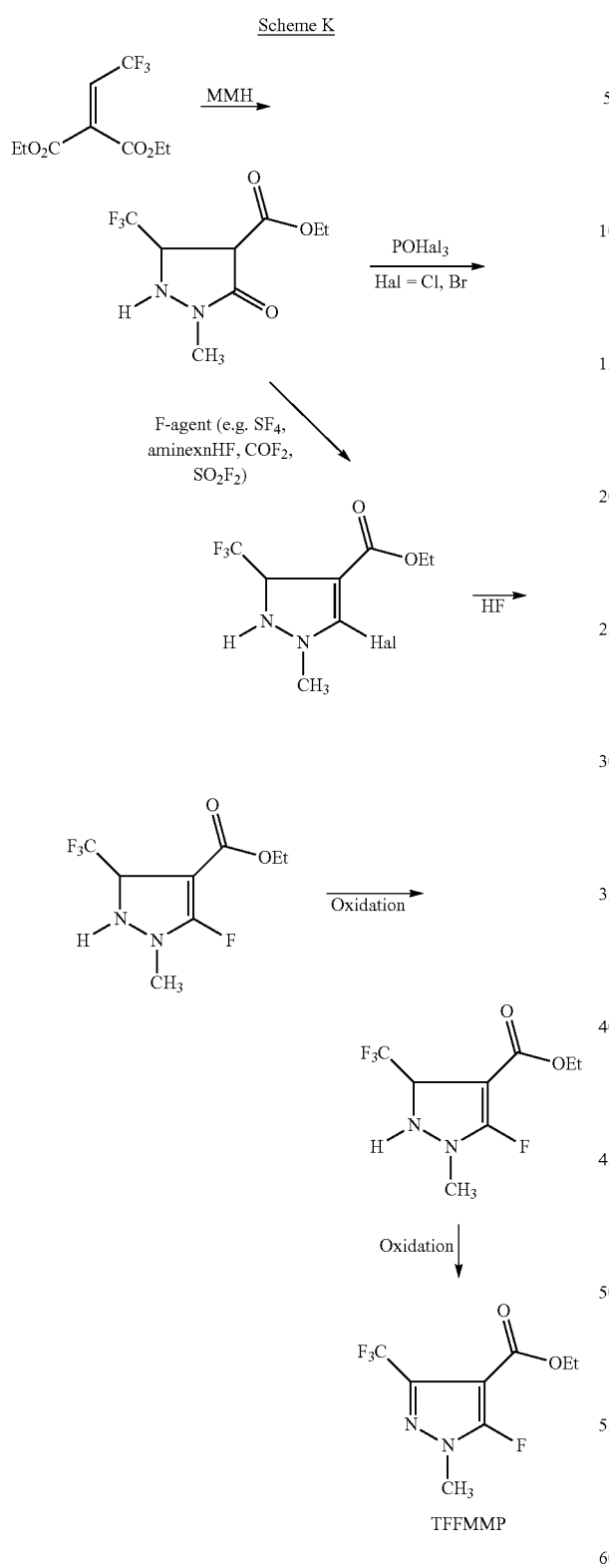

Such 3-halo-pyrazoles, synthesized according to the invention, as described here in the Scheme K, are used in the international patent publication WO 2017/012965 (to Bayer) for increasing the growth of plants, and in the international patent publication WO 2008/101976 as a precursor of fungicides.

The Japanese patent publications JP 2017039722 and JP 2015155399 describe the use of the corresponding $CF_2H$-derivative as precursor of active ingredients for agro, this being prepared analogously, according to the invention, and as shown in following Scheme L.

Scheme L

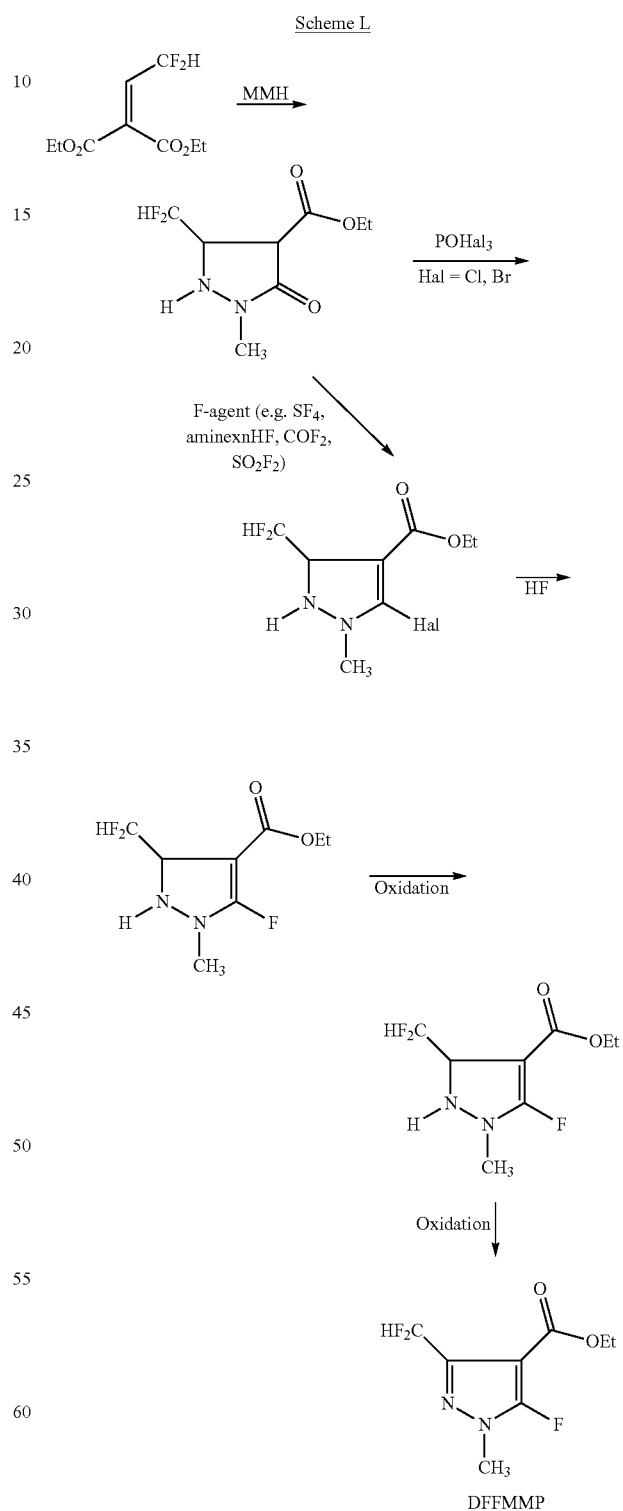

In the international patent publications WO 2012/065945 and WO 2012065932 (both to Bayer), for example, thiocarboxamides are used as starting materials for e.g. fungicides. These are made by reaction with P2S5. According to the invention, these are prepared analogously from DFFMMP and TFFMMP and further converted to the active compounds with carboxamide structure, and as shown in following Scheme M.

WO 2010/037688 describes in batch the reaction of ETFBO with the HCl salt of the hyrazine. The reaction time is 15 h in refluxing methanol, as shown in following Scheme O, the process can also be performed according to the invention.

Scheme M

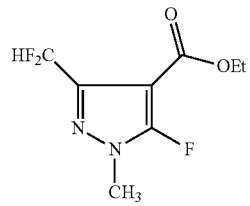

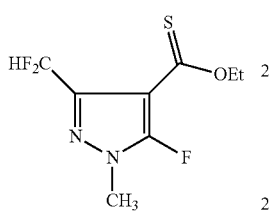

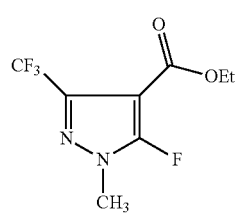

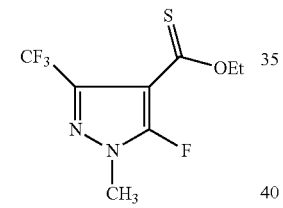

Scheme O

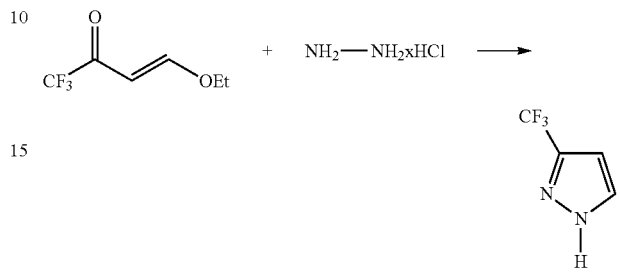

Also, reactions with hydrazine are necessary to produce the intermediates to florasulam and diclosulam. The synthesis, according to the invention, is shown in Scheme P for florasulam.

Scheme Q shows the synthesis, according to the invention, of cloransulam-methyl (diclosulam).

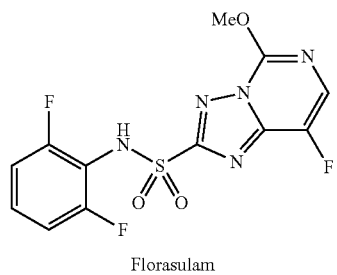

Florasulam

Faming Zhuanli Shenqing (2010), CN 101824000 describes the reaction of ETFBO with MMH. Both isomers are formed, as shown in following Scheme N, but this can be avoided according to the process of invention.

Scheme N

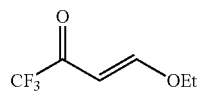 + 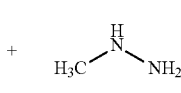 →

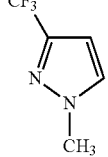 + 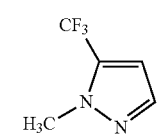

The use of CF3-pyrazoles as starting materials for agrochemicals is described in WO 2007/043677. Early publications are by Schlosser et al. in Journal of Organic Chemistry (2002) (17), 2913-2920, Pavlik, James W. et al. in Journal of Heterocyclic Chemistry (2002), 39 (5), 1025-1027 and in WO 2013/167586.

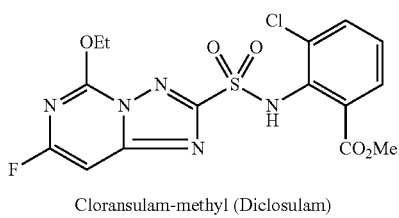

Cloransulam-methyl (Diclosulam)

Scheme P

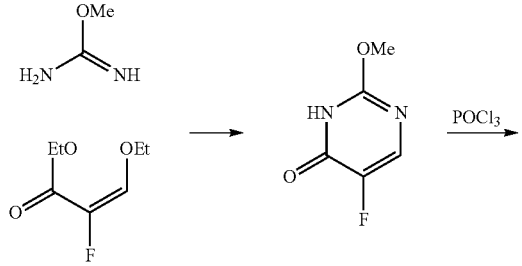

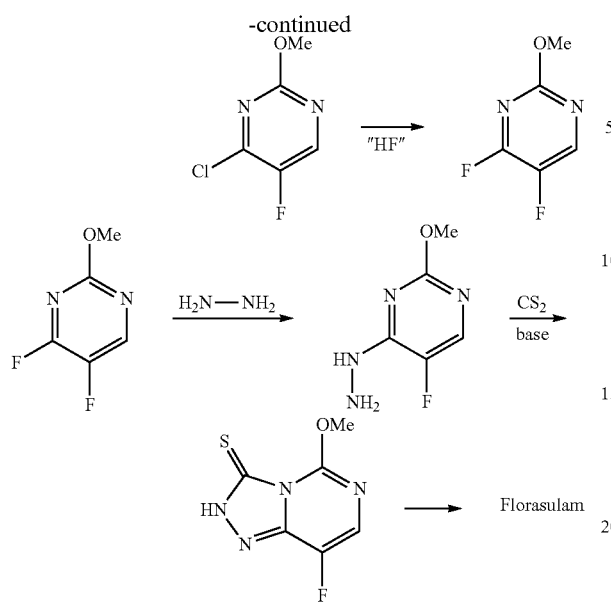

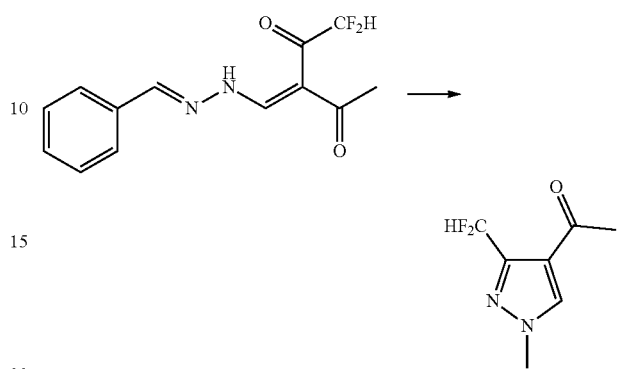

and WO 2012/025469, and wherein the underlying reactions and prepared molecules are detailed, and which references are incorporated herein by reference in their entirety.

WO 2018/024644 (to Solvay):

WO 2009/135808 (to BASF):

With use of a microreactor in the process of the invention the formation of the undesired benzaldehyde methyl hydrazone described therein is avoided since MMH can be used directly and anhydrous, in the microreactor process of the invention.

WO2009/106230/EP 2 133 341 (to Bayer):

This patent publication describes the use of MMH as a hyrazone derivative to obtain high regioselectivity to the desired pyrazole regioisomer. This said derivatization of the MMH to the hyrazone is not necessary when using a microreactor and anhydrous MMH according to the invention, a synthesis step can be saved.

WO 2012/025469 (to Solvay):

There are expensive ionic liquids and e.g. solvents such as 365mfc used as reaction components to achieve a regioisomer formation of up to about 9:1. These solvents must be removed and recycled after the reaction, which is difficult and expensive.

Further Details of the Invention:

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm, or of about ≤4 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in

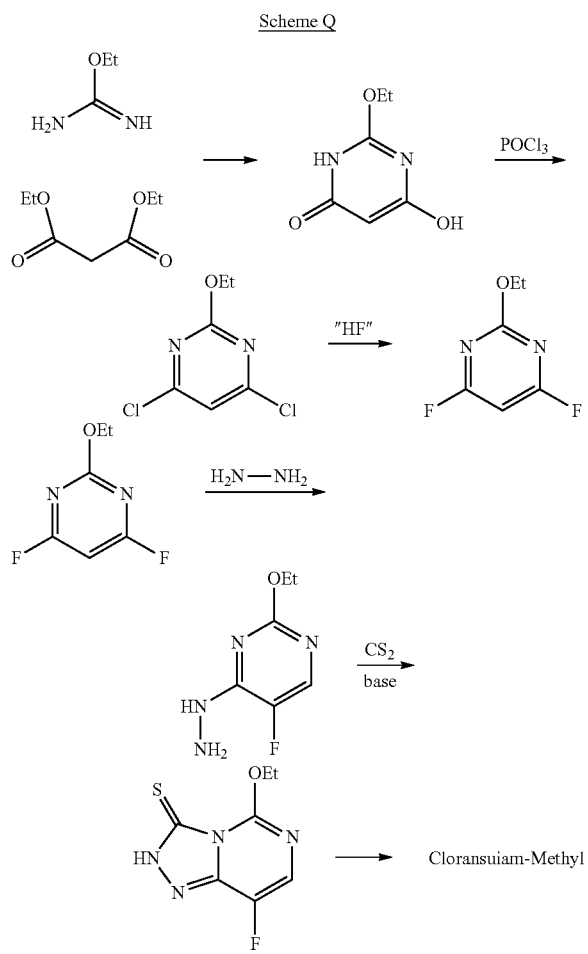

Scheme Q

Further reactions that may be performed according to the invention are shown herein below in by reference to some patent publications, e.g. WO 2018/024644, WO 2009/135808, WO2009/106230 and corresponding EP 2 133 341, question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤5 mm, or of about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤5 mm, or of about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the plug flow reactor and/or a tubular flow reactor, employed in this embodiment of the invention is configured with the construction materials as defined herein for the microreactors. For example, such construction materials are silicium carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic or high grade stainless steel (Inox or Hastelloy) continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

Thus, without being limited to, for example, in an embodiment of the invention the microreactor suitable for, preferably for industrial, production an "SiC-microreactor" that is comprising or is made of SiC (silicium carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld.

In order to meet both the mechanical and chemical demands placed on production scale flow reactors, Plantrix modules are fabricated from 3M™ SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the Chemtrix Protrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0,35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminium), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicium carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the targeted compounds described herein in the context of the invention. If more than one microreactor, preferably more than one SiC-microreactors, are used in the production, preferably in the industrial production, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MHRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$.

In a first embodiment (1), the invention relates to a use of an amine compound of formula (I), R4-NH—X, and/or a monohydrate thereof, wherein
R4 denotes H or a branched or non-branched C1-C4 alkyl group, and
X denotes a NH2 group or C(=NH)—OR5 group, wherein R5 denotes a branched or non-branched C1-C4 alkyl group,
in a process for the manufacture of a fluorinated or non-fluorinated 5- or 6-membered heterocyclic compound containing two nitrogen atoms in the ring system of the said compound, comprising a steps of feeding the said amine compound into at least one continuous flow reactor with upper lateral dimensions of up to about 1 cm, preferably with upper lateral dimensions of up to about ≤5 mm, preferably into at least one microreactor, and therein reacting the said amine compound with a carbonyl group containing three ring-carbon-atom precursor compound for the fluorinated or non-fluorinated 5- or 6-membered heterocyclic compound containing two nitrogen atoms in the ring system.

In a second embodiment (2), the invention relates to a process for the manufacture of a fluorinated or non-fluorinated 5- or 6-membered heterocyclic compound containing two nitrogen atoms in the ring system of the said compound, wherein the process is comprising the steps of:
(a) providing an amine compound of formula (I), R4-NH—X, and/or a monohydrate thereof,
wherein
R4 denotes H or a branched or non-branched C1-C4 alkyl group, and
X denotes a NH2 group or C(=NH)—OR5 group, wherein R5 denotes a branched or non-branched C1-C4 alkyl group,
(b) providing a carbonyl group containing three ring-carbon-atom precursor compound for the fluorinated or non-fluorinated 5- or 6-membered heterocyclic compound containing two nitrogen atoms in the ring system,
(c) feeding the amine compound of (a) and the precursor compound of (b), separately or as a mixture, into at least one continuous flow reactor with upper lateral dimensions of about ≤5 mm, or of about ≤4 mm, preferably into at least one microreactor, and therein
(d) reacting the said amine compound of (a) with the said precursor compound of (b), under cyclisation to obtain a reaction mixture comprising the fluorinated or non-fluorinated 5- or 6-membered heterocyclic compound containing two nitrogen atoms in the ring system, and
(e) withdrawing the reaction mixture obtained in (d) from the said continuous flow reactor, preferably from the microreactor, to yield the fluorinated or non-fluorinated 5- or 6-membered heterocyclic compound containing two nitrogen atoms in the ring system, and
(f) optionally further purifying and/or isolating the fluorinated or non-fluorinated 5- or 6-membered heterocyclic compound containing two nitrogen atoms in the ring system obtained in (e) to yield a purified and/or isolated fluorinated or non-fluorinated 5- or 6-membered heterocyclic compound containing two nitrogen atoms in the ring system.

In a variant of the first embodiment (1) or of the second embodiment (2), the invention relates to the use of an amine compound of formula (I), and/or a monohydrate thereof, according to embodiment (1), or a process according to embodiment (2) for the manufacture of a fluorinated or non-fluorinated 5- or 6-membered heterocyclic compound containing two nitrogen atoms in the ring system according to embodiment (1),
wherein the amine compound is either a hydrazine compound of formula (Ia), R4-NH—NH2, and/or a monohydrate thereof, wherein R4 denotes H or a branched or non-branched C1-C4 alkyl group, preferably hydrazine or methyl hydrazine, or
wherein the amine compound is an amino imidic acid alkyl ester compound of formula (Ib), R4-NH—C(=NH)—OR5, wherein R4 denotes H or a branched or non-branched C1-C4 alkyl group and R5 denotes a branched or non-branched C1-C4 alkyl group, preferably an amino imidic acid methyl ester of formula $H_2N$—C(=NH)—$OCH_3$ [also $H_2N$—C(=NH)—OMe] or an amino imidic acid ethyl ester of formula $H_2N$—C(=NH)—$OCH_2CH_3$ [also $H_2N$—C(=NH)—OEt].
and more preferably, in the said variant of the first embodiment (1) or of the second embodiment (2), wherein the amine compound is either a hydrazine compound of formula (Ia), R4-NH—NH2, and/or a monohydrate thereof, wherein R4 denotes H or a branched or non-branched C1-C4 alkyl group, preferably hydrazine or methyl hydrazine, is water-free.

In a third embodiment (3), the invention relates to a process for the manufacture of a compound according to embodiment (1), wherein the compound is a fluorinated or non-fluorinated 5-membered heterocyclic compound containing two nitrogen atoms in the ring system of the said compound (pyrazole compound), and which is a fluorinated or non-fluorinated pyrazole compound of formula (1)

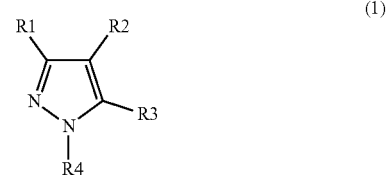

wherein
R1 represents alkyl, haloalkyl, perfluoralkyl;
R2 represents H, $CO_2$-alkyl, $CO_2$-haloalkyl, $CO_2H$, Cl, F, COCl;
R3 represents H, halogen, alkyl, haloalkyl, hydroxyl (—OH), optionally wherein the hydroxyl (—OH) is subject to keto-enol tautomerism and the hydroxyl (—OH) together with the carbon atom to which it is bound and with the adjacent carbon atom constitute an enol-form (C=CH—OH) which equilibrates with the keto-form (CH—C=O) or partially or completely converts to the enol-form (C=CH—OH) to the keto-form (CH—C=O);
R4 represents H, alkyl;
and wherein in each of R1 to R3, independently the term "alkyl" denotes C1-C4-alkyl residue, and independently the term "halo" represents a halogen atom selected from the group consisting of F, Cl, Br, and J, preferably F or Cl, more preferably F;
wherein the process is comprising the steps of:
(a) providing an amine compound of formula (I), R4-NH—X, and/or a monohydrate thereof, wherein
R4 denotes H or a branched or non-branched C1-C4 alkyl group, and
X denotes a NH2 group,
(b) providing a carbonyl group containing three ring-carbon-atom precursor compound for the fluorinated or non-fluorinated pyrazole compound of formula (1),
(c) feeding the amine compound of (a) and the precursor compound of (b), separately or as a mixture, into at least one continuous flow reactor with upper lateral dimensions of about ≤5 mm, preferably into at least one microreactor, and therein
(d) reacting the said amine compound of (a) with the said precursor compound of (b), under cyclisation to obtain a reaction mixture comprising the fluorinated or non-fluorinated pyrazole compound of formula (1), and
(e) withdrawing the reaction mixture obtained in (d) from the said continuous flow reactor, preferably from the microreactor, to yield the fluorinated or non-fluorinated pyrazole compound of formula (1), and
(f) optionally further purifying and/or isolating the fluorinated or non-fluorinated pyrazole compound of formula (1) obtained in (e) to yield a purified and/or isolated fluorinated or non-fluorinated pyrazole compound of formula (1).

Note on R2 and R3: Some of the substituents shown may be formed after the cyclisation by subsequent derivatisation process.

For example, regarding the COCl-group in R2, it is noted that the industrially most important R2 currently is the carboxylic acid chloride (COCl), which is produced in a subsequent stage by reacting the preceding carboxylic acid group resulting from the cyclisation stage with SOCl2).

Also commercially important compounds are 5-fluoropyrazoles (R3=F). Thus, in a subsequent stage suitable substituents R3 resulting from the cyclisation stage in the pyrazoles may be replaced by fluorine (F); and the same is analogously possible for introducing chlorine into R3-position of the pyrazole.

Such derivatizations that may take place in a subsequent step after the cyclisation reaction according to the present invention are exemplified hereunder, as representative illustration but not intending to be limiting, are shown hereunder in the Schemes R and S:

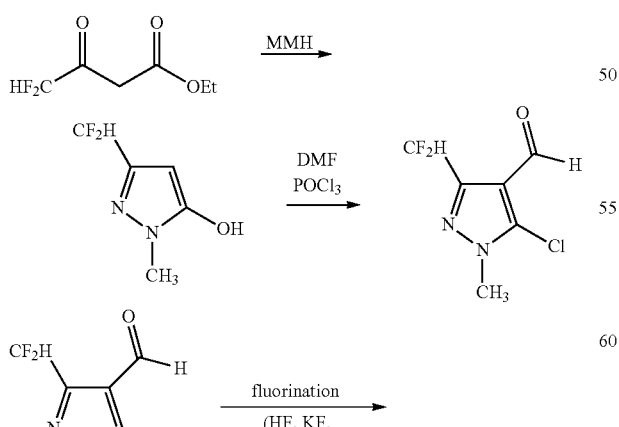

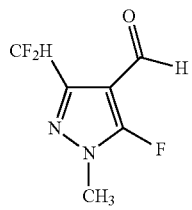

Formula example "derivatization" for R3=halogen, without microreactor, as described in EP 2325173, WO 2011/061205, and WO 2013/171134:
Formula example "derivatization" for R2=COCl, R3=F, as described in WO 2011/061205:

Scheme S

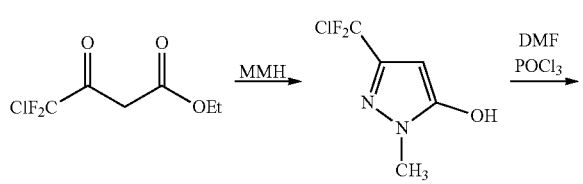

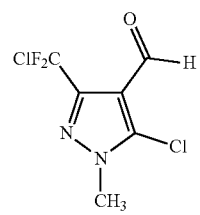

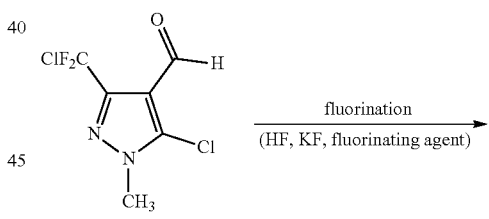

In a fourth embodiment (4), the invention relates to a process for the manufacture of a compound according to embodiment (1), wherein the compound is a fluorinated or non-fluorinated 6-membered heterocyclic compound containing two nitrogen atoms in the ring system of the said compound (pyrimidone compound), and which is a fluorinated or non-fluorinated pyrimidone compound of formula (2)

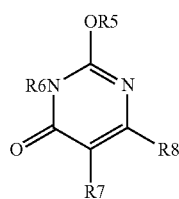

(2)

wherein R5 represents a branched or non-branched C1-C4 alkyl group, preferably a methyl or ethyl group, more preferably a methyl group, wherein R6 represents H, a branched or non-branched C1-C4 alkyl group, preferably H, a methyl or ethyl group, more preferably H or a methyl group, and most preferably H, wherein R7 represents H, halogen, a branched or non-branched C1-C4 alkyl group, preferably H, F, Cl, a methyl or ethyl group, more preferably H, F, Cl or a methyl group, and most preferably H, wherein R8 represents H or hydroxyl (—OH), preferably if R7 is F then R8 is H or if R7 is H then R8 is hydroxyl (—OH), wherein the process is comprising the steps of:
(a) providing an amine compound of formula (I), R4-NH—X, and/or a monohydrate thereof,
wherein
R4 denotes H or a branched or non-branched C1-C4 alkyl group, and
X denotes a C(=NH)—OR5 group, wherein R5 denotes a branched or non-branched C1-C4 alkyl group,
(b) providing a carbonyl group containing three ring-carbon-atom precursor compound for the fluorinated or non-fluorinated 6-membered heterocyclic compound containing two nitrogen atoms in the ring system,
(c) feeding the amine compound of (a) and the precursor compound of (b), separately or as a mixture, into at least one continuous flow reactor with upper lateral dimensions of about ≤5 mm, or of about ≤4 mm, preferably into at least one microreactor, and therein
(d) reacting the said amine compound of (a) with the said precursor compound of (b), under cyclisation to obtain a reaction mixture comprising the fluorinated or non-fluorinated pyrimidone compound of formula (2), and
(e) withdrawing the reaction mixture obtained in (d) from the said continuous flow reactor, preferably from the microreactor, to yield the fluorinated or non-fluorinated pyrimidone compound of formula (2), and
(f) optionally further purifying and/or isolating the fluorinated or non-fluorinated pyrimidone compound of formula (2) obtained in (e) to yield a purified and/or isolated fluorinated or non-fluorinated pyrimidone compound of formula (2).

In a fifth embodiment (5), the invention relates to a use of an amine compound of formula (I), and/or a monohydrate thereof, according to embodiment (1), or a process for the manufacture of a fluorinated or non-fluorinated 5- or 6-membered heterocyclic compound containing two nitrogen atoms in the ring system according to any one of the embodiments (2) to (4), wherein the feeding and reacting takes place in at least one microreactor in step (c) under one or more of the following conditions:
flow rate: of from about 10 ml/h up to about 400 l/h;
temperature: of from about 30° C. up to about 150° C.;
pressure: of from about 5 bar up to about 50 bar;
residence time: of from about 1 second up to about 60 minutes, preferably of from about 1 minute up to about 60 minutes.

In a six embodiment (6), the invention relates to a use of an amine compound of formula (I), and/or a monohydrate thereof, according to embodiment (1) or embodiment (5), or a process for the manufacture of a fluorinated or non-fluorinated 5- or 6-membered heterocyclic compound containing two nitrogen atoms in the ring system according to any one of the embodiments (2) to (5), wherein at least one of the said continuous flow reactors, preferably at least one of the microreactors, in step (c) independently is a SiC-continuous flow reactor, preferably independently is an SiC-microreactor.

In a seventh embodiment (7), the invention relates to a use of an amine compound of formula (I), and/or a monohydrate thereof, according to embodiment (6), or a process for the manufacture of a fluorinated or non-fluorinated 5- or 6-membered heterocyclic compound containing two nitrogen atoms in the ring system according to embodiment (6), wherein the at least one of the microreactors in step (d) independently is an SiC-microreactor, preferably wherein the at least one of the microreactors, in step (d) is an SiC-microreactor in the step (d) as defined in embodiment (1).

In an eights embodiment (8), the invention relates to a use of an amine compound of formula (I), and/or a monohydrate thereof, according to embodiment (1) or any one of embodiments (5) to (7), or a process for the manufacture of a fluorinated or non-fluorinated 5- or 6-membered heterocyclic compound containing two nitrogen atoms in the ring system according to any one of the embodiments (2) to (7), wherein the carbonyl group containing three ring-carbon-atom precursor compound for the manufacture of a fluorinated or non-fluorinated 5- or 6-membered heterocyclic compound containing two nitrogen atoms in the ring system, (i) in case of the manufacture of a fluorinated or non-fluorinated 5-membered heterocyclic compound containing two nitrogen atoms in the ring system, which preferably is a fluorinated or non-fluorinated pyrazole compound of formula (1) as defined in embodiment (3), is a carbonyl group containing three ring-carbon-atom precursor compound selected from the group consisting of one of the following compounds:

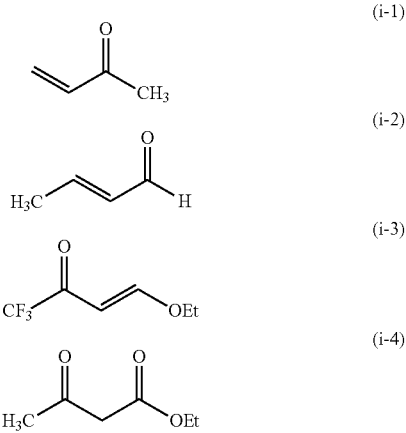

(ii) in case of the manufacture of a fluorinated or non-fluorinated 6-membered heterocyclic compound containing two nitrogen atoms in the ring system, which preferably is a fluorinated or non-fluorinated pyrimidone compound of formula (2) as defined in embodiment (4), is a carbonyl group containing three ring-carbon-atom precursor compound selected from the group consisting of one of the following compounds:

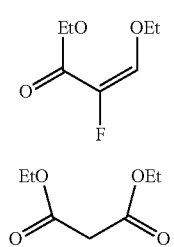

(ii-1)

(ii-2)

wherein in each independently "OEt" F may be replaced by "OMe"

In a variant of the eights embodiment (8), the invention relates to a use of an amine compound of formula (I), and/or a monohydrate thereof, according to embodiment (1) or any one of embodiments (5) to (7), or a process for the manufacture of a fluorinated or non-fluorinated 5- or 6-membered heterocyclic compound containing two nitrogen atoms in the ring system according to any one of the embodiments (2) to (7), wherein the carbonyl group containing three ring-carbon-atom precursor compound for the manufacture of a fluorinated or non-fluorinated 5- or 6-membered heterocyclic compound containing two nitrogen atoms in the ring system, (i) in case of the manufacture of a fluorinated or non-fluorinated 5-membered heterocyclic compound containing two nitrogen atoms in the ring system, which preferably is a fluorinated or non-fluorinated pyrazole compound of formula (1) as defined in embodiment (3), is a carbonyl group containing three ring-carbon-atom precursor compound selected from the group consisting of one of the following compounds:

(a) a compound with the formula (A)

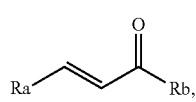

(A)

wherein
Ra and Rb each independently denote H; an O—C1-C4 alkyl (preferably OMe or OEt); C1-C4 alkyl (preferably $CH_3$ (methyl) or $CH_2CH_3$ (ethyl)); C1-C4 haloalkyl (preferably $CF_3$, $CHF_2$, $CCl_3$, $CClF_2$, CHClF, $CH_2F$, $CCl_2F$, $CF_2Br$), C1-C4 alkyl, which may optionally be branched or non-branched and/or may optionally be substituted or unsubstituted; C1-C4 haloalkyl, which may optionally be branched or non-branched and/or may optionally be substituted or unsubstituted;

(b) a compound with the formula (B)

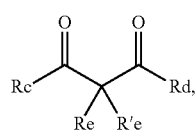

(B)

wherein
Rc and Rd each independently denote H; an O-C1-C4 alkyl (preferably OMe or OEt); C1-C4 alkyl (preferably $CH_3$ (methyl) or $CH_2CH_3$ (ethyl)); C1-C4 haloalkyl (preferably $CF_3$, $CHF_2$, $CCl_3$, $CClF_2$, CHClF, $CH_2F$, $CCl_2F$, $CF_2Br$; C1-C4 alkyl), which may optionally be branched or non-branched and/or may optionally be substituted or unsubstituted; C1-C4 haloalkyl, which may optionally be branched or non-branched and/or may optionally be substituted or unsubstituted;

Re and R'e each denotes a H or together a residue of form a double bond residue of formula =CH-Rx, wherein Rx represents an O-C1-C4 alkyl (preferably OMe or OEt); C1-C4 alkyl (preferably $CH_3$ (methyl) or $CH_2CH_3$ (ethyl)); C1-C4 haloalkyl (preferably $CF_3$, $CHF_2$, $CCl_3$, $CClF_2$, CHClF, $CH_2F$, $CCl_2F$, $CF_2Br$; C1-C4 alkyl), which may optionally be branched or non-branched and/or may optionally be substituted or unsubstituted; C1-C4 haloalkyl, which may optionally be branched or non-branched and/or may optionally be substituted or unsubstituted;

—NRyRz, wherein Ry and Rz independently represent C1-C4 alkyl (preferably $CH_3$ (methyl) or $CH_2CH_3$ (ethyl)), which may optionally be branched or non-branched and/or may optionally be substituted or unsubstituted, C1-C4 haloalkyl (preferably $CF_3$, $CHF_2$, $CCl_3$, $CClF_2$), which may optionally be branched or non-branched and/or may be substituted or unsubstituted, or Ry and Rz together represent a C4-C7 alkyl residue and together with the N to which they are bonded form a 5- to 6-membered heteroalkyl cycle containing one nitrogen atom, which may optionally be branched or non-branched and/or may optionally be substituted or unsubstituted;

(c) a compound selected from the consisting of compounds having one of the following formulae ($C_a$-$C_e$):

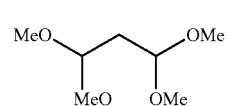

($C_a$)

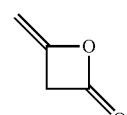

($C_b$)

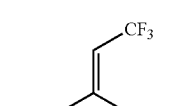

($C_c$)

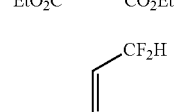

($C_d$)

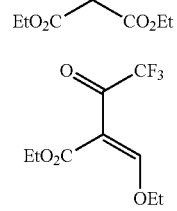

($C_e$)

In a ninth embodiment (9), the invention relates to a use of an amine compound of formula (I), and/or a monohydrate thereof, according to embodiment (1) or any one of embodiments (5) to (8), or a process for the manufacture of a fluorinated or non-fluorinated 5- or 6-membered heterocyclic compound containing two nitrogen atoms in the ring system according to any one of the embodiments (2) to (8), wherein the manufactured fluorinated or non-fluorinated 5- or 6-membered heterocyclic compound containing two nitrogen atoms in the ring system, (i) in case of a fluorinated or non-fluorinated 5-membered heterocyclic compound containing two nitrogen atoms in the ring system, which preferably is a fluorinated or non-fluorinated pyrazole compound of formula (1) as defined in embodiment (3), is selected from the group consisting of one of the following compounds:

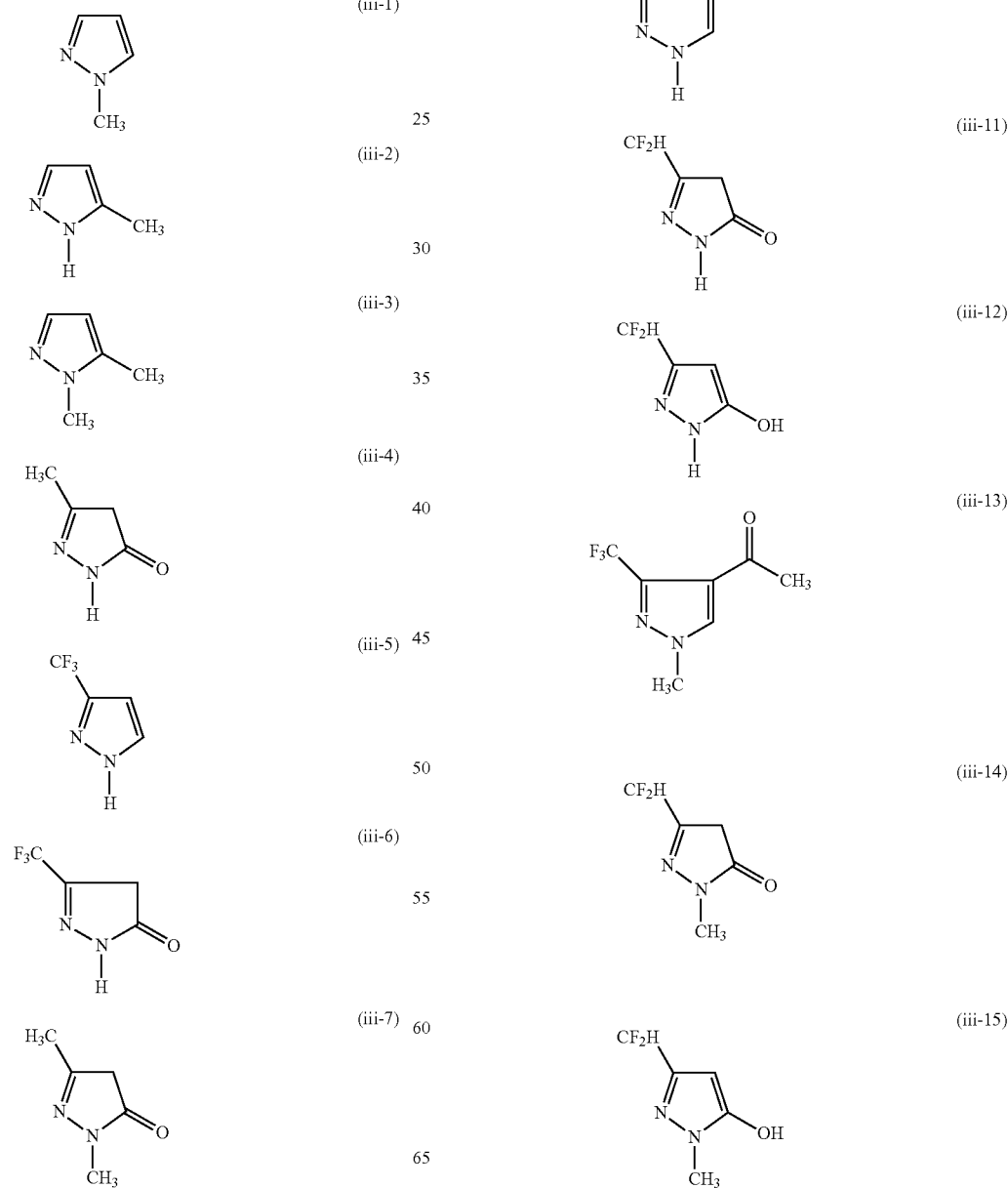

(iii-16)
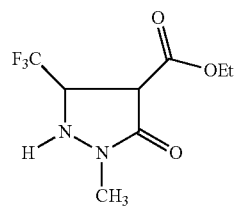
(iii-17)
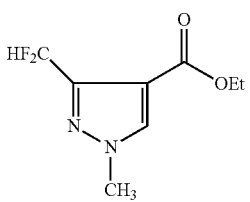
(iii-18)
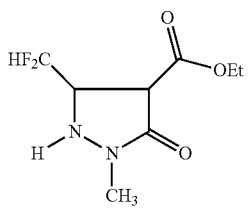
(iii-19)
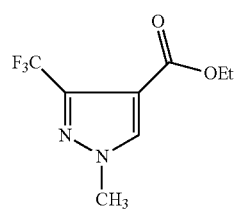
(iii-20)
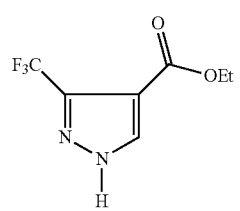
(iii-21)
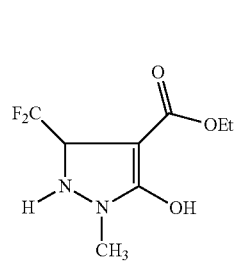
(iii-22)
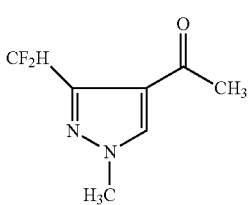
(iii-23)
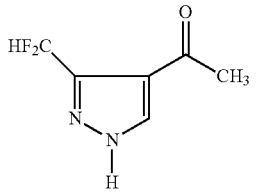
(iii-24)
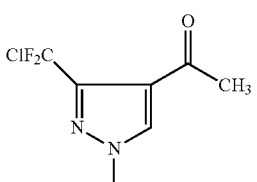
(iii-25)
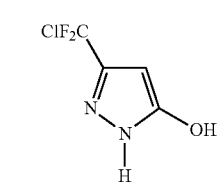
(iii-26)
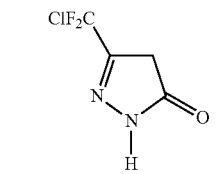
(iii-27)
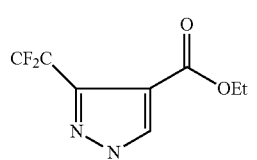
(iii-28)
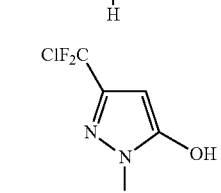
(iii-29)
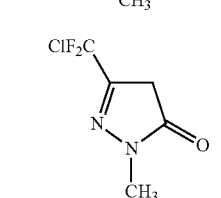
(iii-30)
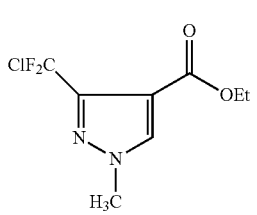
(ii) in ease of a fluorinated or non-fluorinated 6-membered heterocyclic compound containing two nitrogen atoms in the ring system, which preferably is a fluorinated or non-fluorinated pyrimidone compound of formula (2) as defined in embodiment (4), is selected from the group consisting of one of the following compounds:

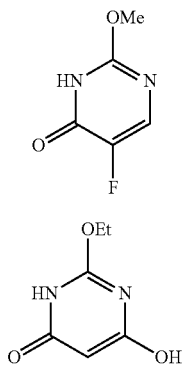

In a tenth embodiment (10), the invention relates to a use of an amine compound of formula (I), and/or a monohydrate thereof, according to embodiment (1) or any one of embodiments (5) to (9), or a process for the manufacture of a fluorinated or non-fluorinated 5- or 6-membered heterocyclic compound containing two nitrogen atoms in the ring system according to any one of the embodiments (2) to (9),
wherein the amine compound is either a hydrazine compound of formula (Ia), R4-NH—NH2, and/or a monohydrate thereof, wherein R4 denotes H or a branched or non-branched C1-C4 alkyl group, preferably hydrazine or methyl hydrazine, or
wherein the amine compound is an amino imidic acid alkyl ester compound of formula (Ib), R4-NH—C(=NH)—OR5, wherein R4 denotes H or a branched or non-branched C1-C4 alkyl group and R5 denotes a branched or non-branched C1-C4 alkyl ester, preferably an amino imidic acid methyl ester of formula H2N—C(=NH)—OCH3 [also H2N—C(=NH)—OMe] or an amino imidic acid ethyl ester of formula H2N—C(=NH)—OCH2CH3 [also H2N—C(=NH)—OEt],
more preferably wherein the amine compound is either a hydrazine compound of formula (Ia), R4-NH—NH2, and/or a monohydrate thereof, wherein R4 denotes H or a branched or non-branched C1-C4 alkyl group, preferably hydrazine or methyl hydrazine, is water-free.

Thus, a particular advantage of the method of the invention is a high conversion and/or high selectivity, and especially both, high conversion and high selectivity.

In FIG. 1, an exemplary embodiment of a process scheme for the manufacture of compounds according to the process of the invention. Although, FIG. 1 exemplifies the use of two microreactors, of course as described above, the first and/or second reactor independently can be a microreactor in combination with a continuous flow reactor with upper lateral dimensions of about ≤5 mm, or of about ≤4 mm, as defined above, or can also be continuous flow reactor with upper lateral dimensions of about ≤4 mm as defined above, without employing a microreactor, e.g. independently a plug flow reactor with upper lateral dimensions of about ≤5 mm, or of about ≤4 mm, and/or tubular flow reactor with upper lateral dimensions of about ≤5 mm, or of about ≤4 mm.

In this exemplary embodiment of FIG. 1, the first microreactor suitable for industrial production is, e.g., made of SiC as offered by Dow Corning as Type G1SiC or Chemtrix MR555 Plantrix (5 to 400 kg per hour) or, e.g. of Hastelloy C as offered by Ehrfeld.

For laboratory search, e.g. on applicable reaction and/or upscaling conditions, for example, as a microreactor the reactor type Plantrix of the company Chemtrix is also suitable as a first and/or as a second microreactor.

The industrial application of the compounds obtained by the process of the invention is once as a raw material for subsequently preparing derivative compounds, and as a raw material for an intermediate for a variety of agrochemicals and pharmaceuticals.

The following examples are intended to further illustrate the invention without limiting its scope.

EXAMPLES

Anhydrous methylhadrazine was prepared as described in U.S. Pat. No. 3,219,550 by FMC with 98% purity. The Chemtrix microreactor type Protrix was made of SiC and had a volume of 27 ml. Hastelloy and stainless steel microreactors such as stainless steel 1.7571 can also be used.

Example 1

Reaction of Difluoroacetoacetate with Orthoformate (Precursor Preparation)

The preparation of EEMDFAA was carried out as e.g. described in WO 2009/106619.

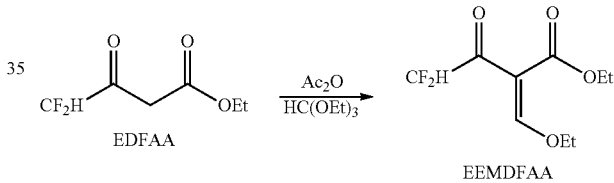

Example 2

Reaction of Ethyl 2-Ethoxymethylene-4,4-Difluoroacetoacetate (EEMDFAA) to Ethyl 3-(Difluoromethyl)-1-Methyl-1H-Pyrazole-4-Carboxylate (DFMMP) in a Microreactor (According to the Invention).

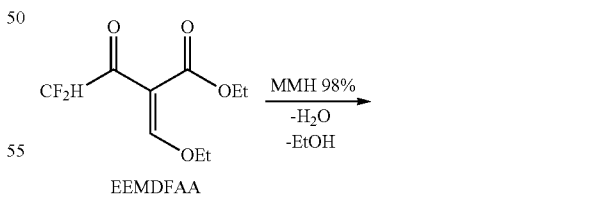

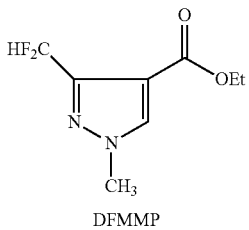

In said Chemtrix 27 ml SiC microreactor, 100 g (0.45 mol) of EEMDFAA and 20.73 g (0.45 mol) of MMH>98% were added per 15 min, and thus continuously at a rate of 400 ml total volume per hour added. The microreactor is tempered before starting up to 30° C., after the warm-up for the start-up phase in the further course of the reaction cooling is now necessary. The turnover is quantitative.

FIG. 2 shows the schematic process performed with MMH (waterfree, >99.0%), in a microreactor, as an example but not intended to be limited to this preferred embodiment. The resulting product DFMMP is purified by distillation, in this embodiment example.

The DFMMP formed without any regioisomer is collected with the resulting reaction products after the microreactor in a collecting vessel as a yellowish oil and then subjected to a solid distillation in vacuo (10-3 Torr). The DFMMP obtained as a white solid had a melting point of 59° C. and a purity>99.0% (GC). The isolated yield was 97%.

Example 3

Reaction of (2,2,2-Trifluoroethylidene)-Propanediacetic Acid Diethyl Ester (Prepared as Described in Journal of the American Chemical Society (1951)73, 3684-6; and U.S. Pat. No. 5,935,966) with Anhydrous MMH (According to the Invention):

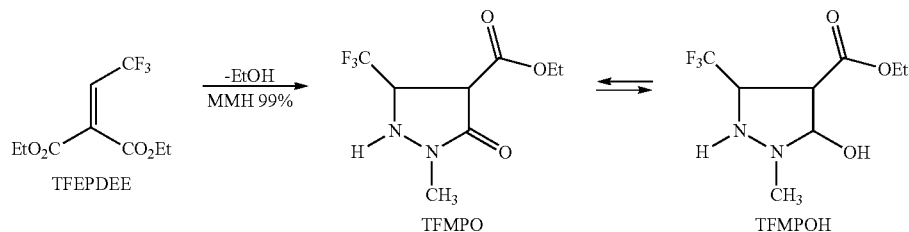

In the Chemtrix 27 ml SiC microreactor, 100 g (0.42 mol) of TFEPDEE (71 ml) and 19.35 g (0.42 mol) of MMH>99% (22 ml) per 15 min, and thus continuously with a Rate of 372 ml total volume added per hour. The microreactor is tempered before starting up to 30° C., after the warm-up for the start-up phase in the further course of the reaction cooling is now necessary. The turnover is quantitative. The crude material obtained as a yellow liquid contains TFPOH at 97%, which gives a yellow liquid with>99% purity (GC) by subsequent fine distillation under high vacuum at 10-3 torr.

TFEPDEE was prepared according to Tetrahedron (2011), 67 (26), 4845-4851 and used at 97% purity.

Example 4

Reaction of 2-Ethoxymethylene-3-Oxo-4,4,4-Trifluorobutyric Acid Ethyl Ester (EMOTFBEE; Prepared as Described in Journal of the American Chemical Society (1951)73, 3684-6; and U.S. Pat. No. 5,935,966) with Anhydrous MMH (According to the Invention):

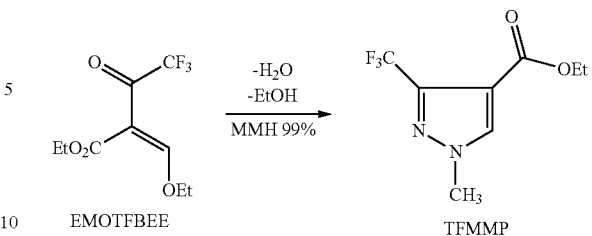

In the Chemtrix 27 ml SiC microreactor, 100 g (0.42 mol) of EMOTFBEE (72 mL) and 19.35 g (0.42 mol) of MMH>99% (22 mL) per 15 min, and thus continuously with a Rate of 376 ml total volume per hour added. The microreactor is tempered before starting up to 30° C. After warming up for the start-up phase, cooling is now necessary in the further course of the reaction. The turnover is quantitative. The material leaving the microreactor, obtained as a yellow liquid, contains the desired product TFMMP with 98% GC purity. By blowing out with N2, ethanol and water are removed and the product solidifies.

Example 5

Solvent-Free Reaction of 2-Ethoxymethylene-3-Oxo-4,4, 4-Trifluorobutyric Acid Ethyl Ester with NH2-NH2×H2O.

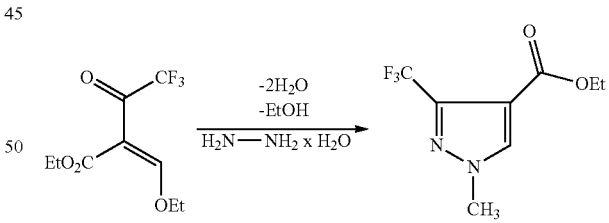

EMOTFBEE

In the 27 ml Chemtrix SiC microreactor, 100 g (0.42 mol) of EMOTFBEE (72 mL) and 21.03 g (0.42 mol) of hydrazine hydrate (21 mL) were added per 15 min. And thus continuously at a rate of 372 ml total volume added per hour. The microreactor is tempered to 100° C. before starting, after the warm-up for the start-up phase cooling is now necessary in the further course of the reaction. The turnover is quantitative. The raw material initially obtained as a partially slowly solidifying liquid contains 97% of ethyl 3-trifluoromethyl-1H-pyrazole-4-carboxylate which gives>98% purity by blowing out with N2 (ethanol and water are still removed). The now determined melting point is 146° C.

Example 6

Reaction of Ethyl Trifluoroacetate (ETFAA) with Anhydrous MMH (According to the Invention):

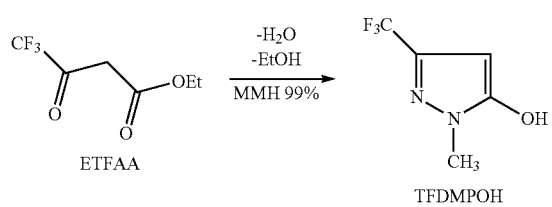

In the 27 ml Chemtrix SiC microreactor, 100 g (0.54 mol) of ETFAA (79 ml) and 24.8 g (0.54 mol) of MMH>99% (28 ml) per 15 min, and thus continuously with a Rate of 428 ml total volume per hour added. The microreactor is tempered before starting up to 30° C.; After warming up for the start-up phase, cooling is now necessary in the further course of the reaction. The turnover is quantitative. The material leaving the microreactor, obtained as a yellowish liquid, already contains the desired product 1-methyl-5-hydroxy-3-trifluoromethylpyrazole (TFDMPOH) with 97% GC purity. By blowing out with N2, ethanol and water are removed and the product solidifies. In contrast to Journal of Heterocyclic Chemistry (1990), 27 (2), 243-5 (14% false regioisomer), the desired product 1-methyl-5-hydroxy-3-trifluoromethylpyrazole (TFDMPOH) is selectively formed in the microreactor.

Example 7

Reaction of Ethyl Trifluoroacetate (ETFAA) with Hydrazine Monohydrate (According to the Invention):

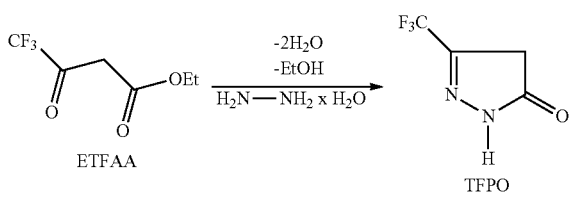

In the Chemtrix 27 ml SiC microreactor, 100 g (0.54 mol) of ETFAA (79 ml) and 27.03 g (0.54 mol) of hydrazine hydrate (27 ml) were added per 15 min in, and thus continuously, at a rate of 424 ml total volume added per hour. The microreactor is tempered before starting up to 120° C.

After warming up for the start-up phase, cooling is now necessary in the further course of the reaction. The turnover is quantitative. The material, which still initially exits as a colorless liquid after the microreactor, already contains the desired product 3-trifluoromethyl 2-pyrazolin-5-one (TFPO) with 98% GC purity (the EtOH with the water has already largely volatilized). By blowing out the partial melt with N 2 at 100° C., residual ethanol and water are removed, after which the product solidifies. The melting point is 210° C.

Example 8

Reaction of Ethyl Acetoacetate (EAA) with Hydrazine Monohydrate (According to the Invention):

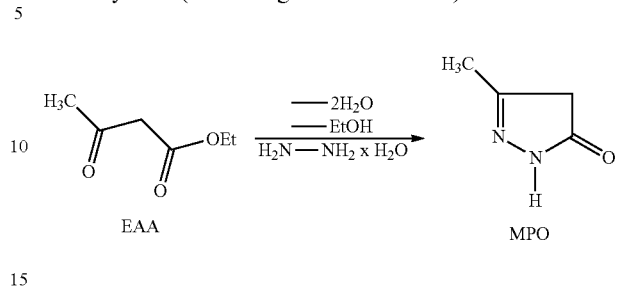

In the 27 ml Chemtrix SiC microreactor, 70.28 g (0.54 mol) of EAA (65.5 ml) and 27.03 g (0.54 mol) of hydrazine hydrate (27 ml) of hydrazine hydrate per 15 min and thus continuously charging the reactor at a rate of 370 ml total volume per hour. The microreactor is tempered before starting up to 120° C.; After warming up for the start-up phase, cooling is now necessary in the further course of the reaction. The turnover is quantitative. The first material, which usually still leaves as a colorless slurry after the microreactor, already contains the desired product 3-methyl-1H-4,5-dihydropyrazol-5-one (MPO) with 96% GC purity. By blowing out with N2, ethanol and water are removed, after which the product is completely solidified. The melting point is 226° C. To obtain more uniform crystals recrystallization would be appropriate but not necessary for the production.

Example 9

Reaction of Acetoacetic Ester (EAA) with Hydrazine Monohydrate (According to the Invention):

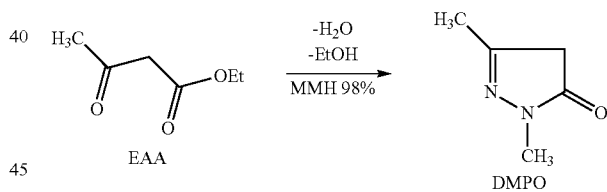

In the 27 ml Chemtrix SiC microreactor, 70.28 g (0.54 mol) EAA (65.5 ml) and 24.8 g (0.54 mol) MMH>99% (28 ml) per 15 min and thus added continuously at a rate of 374 ml total volume per hour. The microreactor is tempered before starting up to 40° C. After warming up for the start-up phase, cooling is now required again in the further course of the reaction. The conversion is quantitative to 1,3-dimethyl-2-pyrazolin-5-one (DMPO). The melting point is 116° C.

DMPO is used for example for Bayer's herbicides Benzophenap and Pyrasulfotole and Mitsui's Pyrazolynate.

Example 10

Reaction of 4,5-Difluoro-2-Methoxy-Pyrimidines with Hydrazine×H2O the 4,5-Difluoro-2-Methoxy-Pyrimidines (and the Pyrimidines in Example 11 and 12) are Precursors of Florasulams and are Prepared and Used Analogously to EP0343752, US 19910744149/U.S. Pat. No. 5,163,995 and Also CN104725323 with 97% Purity.

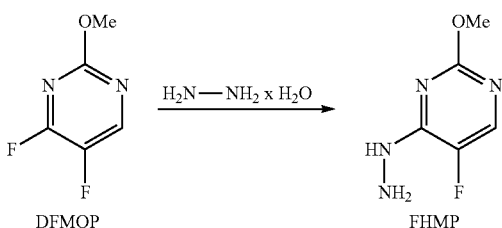

In the 27 ml Chemtrix SiC microreactor, 100 g (0.68 mol) of DFMOP were taken up in 50 ml of MeOH and metered into the microreactor together with 34.04 g (0.68 mol) of hydrazine hydrate per 15 min. The microreactor is tempered before starting up to 70° C.; After warming up for the start-up phase, cooling is now required again in the further course of the reaction. The conversion is quantitative to 5-fluoro-4-hydrazinyl-2-methoxypyrimidines (FHMP). The solvent and HF are removed very carefully in vacuo. The remaining residue FHMP is recrystallized from MeOH to obtain better crystals, alternatively, the FHMP can be used directly after stripping the Me-OH/TI mixture for florasulam.

Example 11

Use of 5-Fluoro-2,4-Dimethoxypyrimidines, Carrying Out Analogously to Example 10

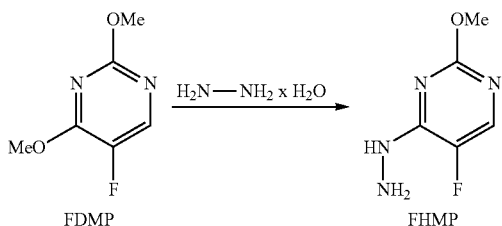

100 g (0.63 mol) of FDMF and 31.53 g (0.63 mol) of hydrazine hydrate were used. Conversations were also quantitative.

Example 12

Use of 4-Chloro-5-Fluoro-2-Methoxypyrimidines, Carrying Out Analogously to Example 10

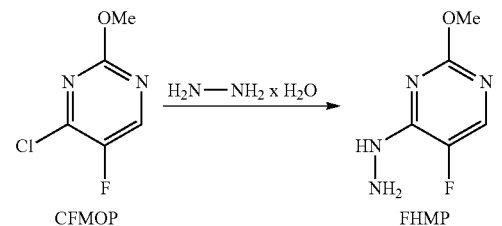

100 g (0.61 mol) of 4-chloro-5-fluoro-2-methoxypyrimidines (CFMOP) and 31.53 g (0.63 mol) of hydrazine hydrate were used. Conversion was also quantitative.

Example 13

Reaction of Chlorodifluoroacetoacetate with Orthoformate (Precursor Preparation)

The preparation of EEMCIDFAA was carried out with slight modifications given hereunder but as in principle described in WO 2012010692 and Organic Process Research & Development (2014), 18(8), 1055-1059.

A solution of ethyl 4-chloro-4,4-difluoro-3-oxo-butanoate (19 g, 95 mmol), triethyl orthoformate (28 g, 190 mmol) and acetic anhydride (29 g, 284 mmol) were heated to 100 to 120° C. with continuous removal of the low boilers, like ethyl acetate produced. After 5 h the low volatility components are removed in vacuum yield more or less quantitative, although during distillation of the product variable yields are observed. Ethyl 2-(ethoxymethylene)-4-chloro-4,4-difluoro-3-oxobutanoate which was distilled at 0.01 Torr in vacuum to yield 93% of EEMCIDFAA.

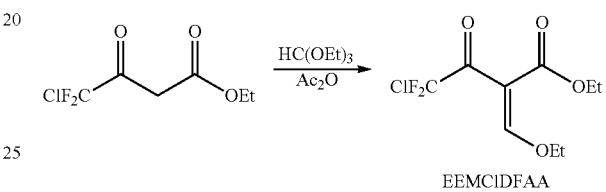

Example 14

Reaction of Ethyl 2-Ethoxymethylene-4,4-Chlorodifluoroacetoacetate (EEMCIDFAA) to Ethyl 3-(Chlorodifluoromethyl)-1-Methyl-1H-Pyrazole-4-Carboxylate (CDFMMP) in a Microreactor (According to the Invention).

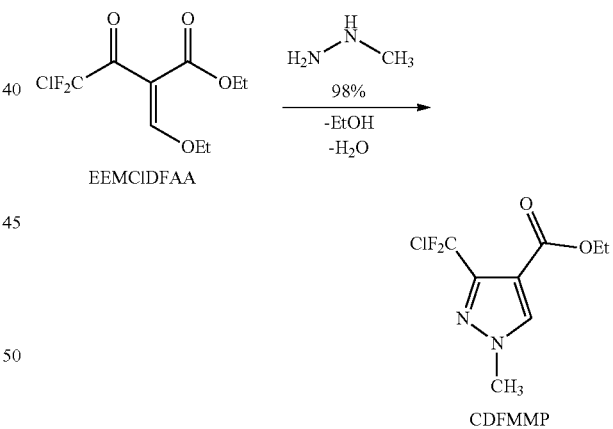

In said Chemtrix 27 ml SiC microreactor, 100 g (0.39 mol) of EEMCIDFAA and 17.97 g (0.39 mol) of MMH>98% were added per 15 min, and thus continuously at a rate of 400 ml total volume per hour added. The microreactor is tempered before starting up to 90° C., after the warm-up for the start-up phase in the further course of the reaction cooling is now necessary. The turnover is quantitative.

FIG. 3 shows the schematic process performed with MMH (waterfree, >98.0%), in a microreactor, as an example but not intended to be limited to this preferred embodiment. The resulting product CDFMMP is purified by distillation, in this embodiment example.

The CDFMMP is formed without any regioisomer and is collected with the resulting reaction products after the microreactor in a collecting vessel as a yellowish oil with crystalline particles and then subjected to a distillation (with a heated condenser to avoid clogging) in vacuum (10-3 Torr). The CDFMMP obtained at a transition temperature of 150° C. (Oil bath for heating with 195° C.) finally as a white solid after cooling down. The isolated yield was 98%.

What is claimed is:

1. A process for manufacture of a fluorinated or non-fluorinated 5-membered heterocyclic compound containing two nitrogen atoms in the ring system of the said compound; wherein the compound is a fluorinated or non-fluorinated pyrazole compound of formula (1)

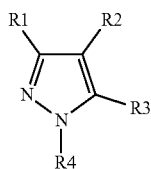

(1)

wherein
R1 represents alkyl, haloalkyl, perfluoralkyl;
R2 represents $CO_2$-alkyl, $CO_2$-haloalkyl, $CO_2H$;
R3 represents H, halogen, alkyl, haloalkyl, hydroxyl (—OH), wherein the hydroxyl (—OH) is subject to keto-enol tautomerism and the hydroxyl
  (—OH) together with the carbon atom to which it is bound and with the adjacent carbon atom constitute an enol-form (C=CH—OH) which equilibrates with the keto-form (CH—C=O) or partially or completely converts to the enol-form (C=CH—OH) to the keto-form (CH—C=O);
R4 represents H, alkyl;
and wherein in each of R1 to R3, independently the term "alkyl" denotes C1-C4-alkyl residue, and independently the term "halo" represents a halogen atom selected from the group consisting of F and Cl;
wherein the process is comprising the steps of:
(a) providing an amine compound of formula (I), R4-NH—X, and/or a monohydrate thereof, wherein R4 denotes H or a branched or non-branched C1-C4 alkyl group, and
X denotes a $NH_2$ group,
(b) providing a carbonyl group containing three ring-carbon-atom precursor compound for the fluorinated or non-fluorinated pyrazole compound of formula (1),
(c) feeding the amine compound of (a) and the precursor compound of (b), separately or as a mixture, into at least one continuous flow reactor with upper lateral dimensions of about ≤5 mm, and therein
(d) reacting the said amine compound of (a) with the said precursor compound of (b), under cyclisation to obtain a reaction mixture comprising the fluorinated or non-fluorinated pyrazole compound of formula (1), and
(e) withdrawing the reaction mixture obtained in (d) from the said continuous flow reactor to yield the fluorinated or non-fluorinated pyrazole compound of formula (1), and
(f) purifying and/or isolating the fluorinated or non-fluorinated pyrazole compound of formula (1) obtained in (e) to yield a purified and/or isolated fluorinated or non-fluorinated pyrazole compound of formula (1).

2. A process for manufacture of a fluorinated or non-fluorinated 6-membered heterocyclic compound containing two nitrogen atoms in the ring system of the said compound; wherein the compound is a fluorinated or non-fluorinated pyrimidone compound of formula (2)

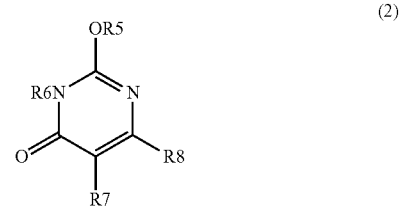

(2)

wherein R5 represents a branched or non-branched C1-C4 alkyl group,
wherein R6 represents H, or a branched or non-branched C1-C4 alkyl group,
wherein R7 represents H, halogen, or a branched or non-branched C1-C4 alkyl group
wherein if R7 is F then R8 is H or if R7 is H then R8 is hydroxyl (—OH),
wherein the process is comprising the steps of:
(a) providing an amine compound of formula (I), R4-NH—X, and/or a monohydrate thereof, wherein R4 denotes H or a branched or non-branched C1-C4 alkyl group, and
X denotes a C(=NH)—OR5 group, wherein R5 denotes a branched or non-branched C1-C4 alkyl group,
(b) providing a carbonyl group containing three ring-carbon-atom precursor compound for the fluorinated or non-fluorinated 6-membered heterocyclic compound containing two nitrogen atoms in the ring system,
(c) feeding the amine compound of (a) and the precursor compound of (b), separately or as a mixture, into at least one continuous flow reactor with upper lateral dimensions of about ≤5 mm, and therein
(d) reacting the said amine compound of (a) with the said precursor compound of (b), under cyclisation to obtain a reaction mixture comprising the fluorinated or non-fluorinated pyrimidone compound of formula (2), and
(e) withdrawing the reaction mixture obtained in (d) from the said continuous flow reactor to yield the fluorinated or non-fluorinated pyrimidone compound of formula (2), and
(f) purifying and/or isolating the fluorinated or non-fluorinated pyrimidone compound of formula (2) obtained in (e) to yield a purified and/or isolated fluorinated or non-fluorinated pyrimidone compound of formula (2).

3. The process for manufacture of compound according to claim 1, wherein the feeding and reacting takes place in step (c) under one or more of the following conditions:
flow rate: of from about 10 ml/h up to about 400l/h;
temperature: of from about 30° C. up to about 150° C.;
pressure: of from about 5 bar up to about 50 bar;
residence time: of from about 1 second up to about 60 minutes.

4. The process for manufacture of compound according to claim 1, wherein at least one of the said continuous flow reactors in step (c) independently is a SiC-continuous flow reactor.

5. The process for manufacture of compound according to claim 1, wherein the carbonyl group containing three ring-carbon-atom precursor compound is selected from the group consisting of one of the following compounds:

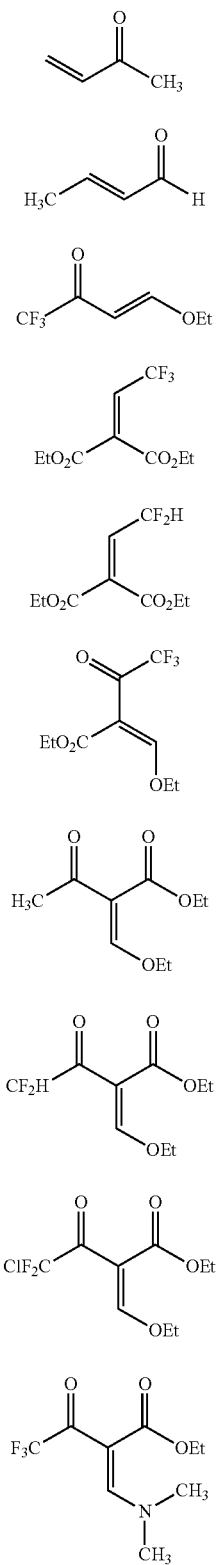

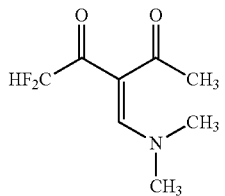

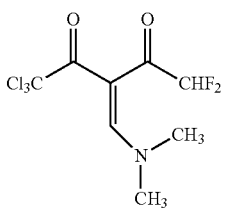

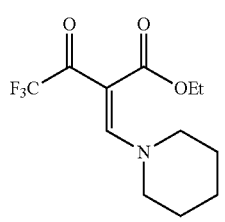

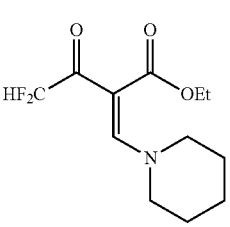

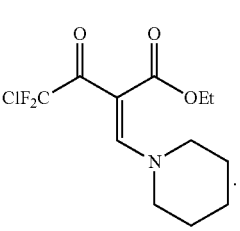

6. The process for manufacture of compound according to claim 1,
wherein the manufactured fluorinated or non-fluorinated 5-membered heterocyclic compound containing two nitrogen atoms in the ring system
is selected from the group consisting of one of the following compounds:

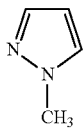

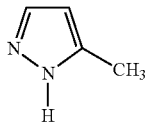

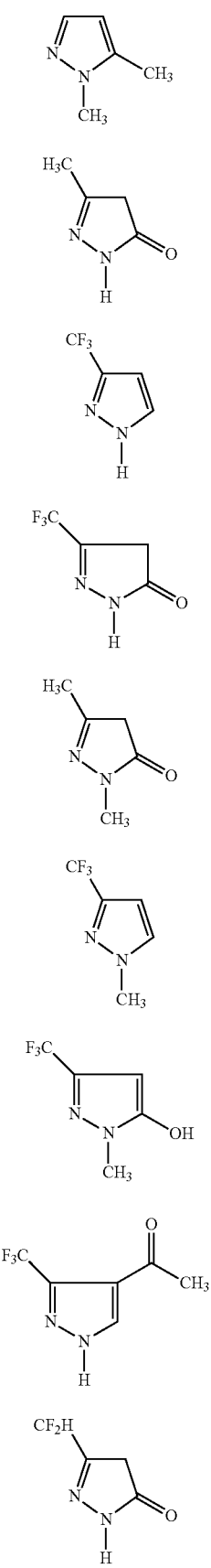

(iii-20) 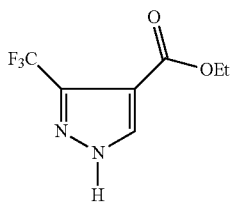

(iii-21) 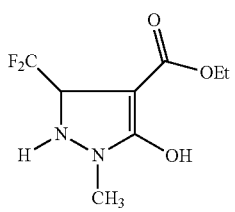

(iii-22) 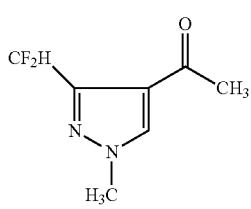

(iii-23) 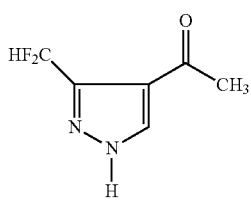

(iii-24) 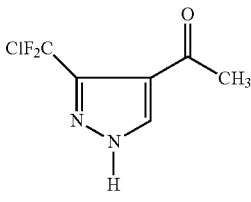

(iii-25) 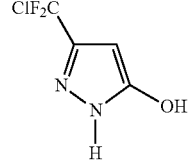

(iii-26) 

(iii-27) 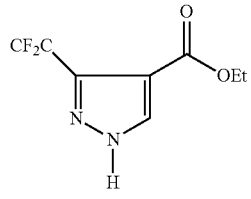

(iii-28) 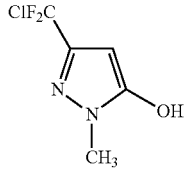

(iii-29) 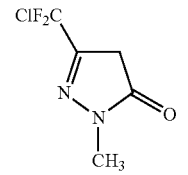

(iii-30) 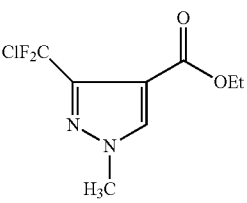

7. The process for manufacture of compound containing according to claim 1, wherein the amine compound is an amino imidic acid alkyl ester compound of formula (Ib), R4-NH—C(=NH)—OR5, wherein R4 denotes H or a branched or non-branched C1-C4 alkyl group and R5 denotes a branched or non-branched C1-C4 alkyl group.

8. The process for manufacture of compound according to claim 2, wherein the carbonyl group containing three ring-carbon-atom precursor compound is selected from the group consisting of one of the following compounds:

(ii-1) 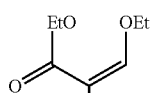

(ii-2) 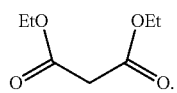

9. The process for manufacture of compound according to claim 2, wherein the manufactured fluorinated or non-fluorinated 6-membered heterocyclic compound containing two nitrogen atoms in the ring system is selected from the group consisting of one of the following compounds:

(iv-1) 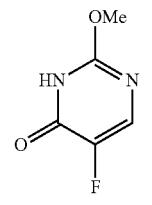

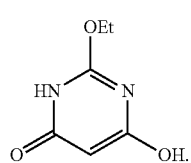

(iv-2)

10. The process for manufacture of compound containing according to claim 1, wherein the amine compound is either a hydrazine compound of formula (Ia), R4-NH—NH$_2$, and/or a monohydrate thereof, wherein R4 denoting H or a branched or non-branched C1-C4 alkyl group is water-free.

11. The process for manufacture of compound containing according to claim 2, wherein the amine compound is an amino imidic acid alkyl ester compound of formula (Ib), R4-NH—C(=NH)—OR5, wherein R4 denotes H or a branched or non-branched C1-C4 alkyl group and R5 denotes a branched or non-branched C1-C4 alkyl group.

12. The process for manufacture of compound containing according to claim 2, wherein the amine compound is either a hydrazine compound of formula (Ia), R4-NH—NH$_2$, and/or a monohydrate thereof, wherein R4 denoting H or a branched or non-branched C1-C4 alkyl group is water-free.

13. The process for manufacture of compound according to claim 2, wherein at least one of the said continuous flow reactors in step (c) independently is a SiC-continuous flow reactor.

\* \* \* \* \*